US012350354B2

(12) United States Patent
Pan et al.

(10) Patent No.: US 12,350,354 B2
(45) Date of Patent: *Jul. 8, 2025

(54) CORE SHELL SILICA PARTICLES AND USE FOR MALODOR REDUCTION

(71) Applicant: Colgate-Palmolive Company, New York, NY (US)

(72) Inventors: Guisheng Pan, Philadelphia, PA (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/614,050

(22) Filed: Mar. 22, 2024

(65) Prior Publication Data

US 2024/0238175 A1 Jul. 18, 2024

Related U.S. Application Data

(63) Continuation of application No. 18/169,367, filed on Feb. 15, 2023, now Pat. No. 11,951,196, which is a continuation of application No. 15/106,426, filed as application No. PCT/US2014/071304 on Dec. 18, 2014, now Pat. No. 11,602,495.

(60) Provisional application No. 61/918,938, filed on Dec. 20, 2013, provisional application No. 61/918,925, filed on Dec. 20, 2013.

(51) Int. Cl.
| | | |
|---|---|---|
| *A61K 8/25* | (2006.01) | |
| *A61K 8/02* | (2006.01) | |
| *A61K 8/19* | (2006.01) | |
| *A61K 8/46* | (2006.01) | |
| *A61Q 11/00* | (2006.01) | |
| *C01B 33/18* | (2006.01) | |
| *C03C 15/00* | (2006.01) | |
| *C03C 17/22* | (2006.01) | |
| *C03C 17/23* | (2006.01) | |
| *C09C 1/30* | (2006.01) | |
| *C09K 3/14* | (2006.01) | |

(52) U.S. Cl.
CPC ................ *A61K 8/25* (2013.01); *A61K 8/022* (2013.01); *A61K 8/0241* (2013.01); *A61K 8/0245* (2013.01); *A61K 8/0258* (2013.01); *A61K 8/19* (2013.01); *A61K 8/466* (2013.01); *A61Q 11/00* (2013.01); *C01B 33/18* (2013.01); *C03C 15/00* (2013.01); *C03C 17/22* (2013.01); *C03C 17/23* (2013.01); *C09C 1/3054* (2013.01); *C09K 3/1436* (2013.01); *C09K 3/1445* (2013.01); *A61K 2800/28* (2013.01); *A61K 2800/621* (2013.01); *A61K 2800/651* (2013.01); *A61K 2800/92* (2013.01); *C01P 2004/61* (2013.01); *C01P 2004/84* (2013.01)

(58) Field of Classification Search
CPC .. A61K 8/25; A61K 8/02; C03C 17/23; C09C 1/30; A61Q 11/00
USPC ..................................................... 424/49, 401
See application file for complete search history.

(56) References Cited

U.S. PATENT DOCUMENTS

| | | | |
|---|---|---|---|
| 2,885,366 | A | 5/1959 | Iler |
| 2,913,419 | A | 11/1959 | Alexander |
| 3,537,815 | A | 11/1970 | Burke, Jr. |
| 3,655,578 | A | 4/1972 | Yates |
| 3,725,095 | A | 4/1973 | Weidman et al. |
| 3,924,030 | A | 12/1975 | Tatara et al. |
| 4,038,380 | A | 7/1977 | Cordon |
| 4,100,269 | A | 7/1978 | Pader |
| 4,336,245 | A | 6/1982 | Wason |
| 4,340,583 | A | 7/1982 | Wason |
| 4,568,540 | A | 2/1986 | Akira et al. |
| 5,413,844 | A | 5/1995 | Persello |
| 5,512,094 | A | 4/1996 | Linton |
| 5,537,363 | A | 7/1996 | Holcomb |
| 5,585,037 | A | 12/1996 | Linton |
| 5,658,573 | A | 8/1997 | Holcomb |
| 5,698,327 | A | 12/1997 | Persello |
| 5,776,435 | A | 7/1998 | Gaffar et al. |
| 5,871,720 | A | 2/1999 | Albanese et al. |
| 5,948,383 | A | 9/1999 | Kuznicki et al. |

(Continued)

FOREIGN PATENT DOCUMENTS

| | | |
|---|---|---|
| CN | 86102002 | 10/1986 |
| CN | 1221393 | 6/1999 |

(Continued)

OTHER PUBLICATIONS

Alexei Smirnov, "Judge Paine hands down Holcomb Healthcare opinion." The Nashville Post, https://www.nashvillepost.com/business/health-care/nnedical-devices/article/20449550/judge-paine-hands-down-holcomb-healthcare-opinion downloaded Dec. 9, 2020, originally published Dec. 16, 2004, pp. 1-2. (Year: 2004).

(Continued)

*Primary Examiner* — Walter E Webb

(57) ABSTRACT

The present invention relates to core shell silica particles, wherein each core shell silica particle comprises a silica core, and a surface of the silica core is etched with metal silicate, the core shell silica particles prepared by: i) admixing an amount of silica particles in water with an amount of a base, wherein the base comprises a monovalent metal ion, to produce core shell silica particles, each core shell silica particle comprising a silica core, and a surface of the silica core etched with a silicate of the monovalent metal ion; and ii) reacting the core shell silica particles formed in step i) with a metal salt comprising a second metal ion, to form core shell silica particles comprising silicate of the second metal ion on the surface of the silica core.

20 Claims, 4 Drawing Sheets

(56) References Cited

U.S. PATENT DOCUMENTS

| | | |
|---|---|---|
| 6,030,222 A | 2/2000 | Tarver |
| 6,121,315 A | 9/2000 | Nair et al. |
| 6,221,326 B1 | 4/2001 | Amiche |
| 6,303,104 B1 | 10/2001 | Winston et al. |
| 6,632,853 B2 | 10/2003 | Alkemper et al. |
| 6,660,380 B1 | 12/2003 | Ishida et al. |
| 6,664,254 B1 | 12/2003 | Rogozinski |
| 7,125,432 B2 | 10/2006 | Huang |
| 7,176,172 B2 | 2/2007 | Harding et al. |
| 7,267,814 B2 | 9/2007 | McGill et al. |
| 7,297,327 B2 | 11/2007 | Pilch et al. |
| 7,402,416 B2 | 7/2008 | Szeles et al. |
| 7,857,985 B2 | 12/2010 | Ishima et al. |
| 8,118,898 B2 | 2/2012 | Wakamiya et al. |
| 8,221,791 B1 | 7/2012 | Santra |
| 8,557,228 B2 | 10/2013 | Pan et al. |
| 8,609,068 B2 | 12/2013 | Hagar et al. |
| 8,834,857 B1 | 9/2014 | Winston et al. |
| 8,840,911 B2 | 9/2014 | Flugge-Berendes et al. |
| 9,028,605 B2 | 5/2015 | Hagar et al. |
| 9,138,600 B2 | 9/2015 | Batchelor et al. |
| 9,375,398 B2 | 6/2016 | Dreher |
| 9,744,112 B2 | 8/2017 | Szewczyk et al. |
| 9,763,861 B2 | 9/2017 | Lei et al. |
| 10,064,794 B2 | 9/2018 | Xu et al. |
| 10,285,920 B2 | 5/2019 | Naser et al. |
| 10,300,028 B2 | 5/2019 | Tuffley |
| 10,369,091 B2 | 8/2019 | Pan et al. |
| 10,532,012 B2 | 1/2020 | Tang et al. |
| 10,596,084 B2 | 3/2020 | Maloney et al. |
| 10,709,907 B2 | 7/2020 | Pan et al. |
| 11,324,678 B2 | 5/2022 | Pan et al. |
| 11,400,032 B2 | 8/2022 | Maloney et al. |
| 11,602,495 B2 | 3/2023 | Pan et al. |
| 11,890,362 B2 | 2/2024 | Tang et al. |
| 11,951,196 B2 | 4/2024 | Pan et al. |
| 2001/0031744 A1 | 10/2001 | Kosbab |
| 2002/0168324 A1 | 11/2002 | Amiche et al. |
| 2003/0206936 A1 | 11/2003 | Barclay et al. |
| 2005/0112161 A1 | 5/2005 | Luo et al. |
| 2006/0034780 A1 | 2/2006 | Guan et al. |
| 2006/0110307 A1 | 5/2006 | McGill et al. |
| 2006/0283095 A1 | 12/2006 | Mahulikar et al. |
| 2007/0003465 A1 | 1/2007 | Huang |
| 2007/0003509 A1 | 1/2007 | Rawlings |
| 2007/0086960 A1 | 4/2007 | Tarver et al. |
| 2007/0275257 A1 | 11/2007 | Muraguchi et al. |
| 2008/0124295 A1 | 5/2008 | Duranton et al. |
| 2008/0152599 A1 | 6/2008 | Brignoli et al. |
| 2009/0203820 A1 | 8/2009 | Sawada et al. |
| 2010/0189663 A1 | 7/2010 | Gallis et al. |
| 2011/0206749 A1 | 8/2011 | Gallis et al. |
| 2012/0021034 A1 | 1/2012 | Zink et al. |
| 2012/0052025 A1 | 3/2012 | Porter et al. |
| 2013/0129642 A1 | 5/2013 | Joiner et al. |
| 2013/0280409 A1 | 10/2013 | Mushock et al. |
| 2016/0296434 A1 | 10/2016 | Fei et al. |
| 2016/0331653 A1 | 11/2016 | Maloney et al. |
| 2016/0331663 A1 | 11/2016 | Maloney et al. |
| 2016/0338919 A1 | 11/2016 | Pan et al. |
| 2017/0266092 A1 | 9/2017 | Maloney et al. |
| 2018/0168965 A1 | 6/2018 | Kocinska et al. |
| 2019/0336419 A1 | 11/2019 | Pan et al. |
| 2020/0282240 A1 | 9/2020 | Pan et al. |
| 2022/0265535 A1 | 8/2022 | Pan et al. |
| 2023/0263711 A1 | 8/2023 | Pan et al. |

FOREIGN PATENT DOCUMENTS

| | | |
|---|---|---|
| CN | 1625383 | 6/2005 |
| CN | 1695447 | 11/2005 |
| CN | 1739483 | 3/2006 |
| CN | 103274422 | 9/2013 |
| CN | 103342368 | 10/2013 |
| CN | 103429250 | 12/2013 |
| DE | 102013216381 | 2/2015 |
| EP | 0345116 | 12/1989 |
| EP | 1935395 | 6/2008 |
| GB | 804486 | 11/1958 |
| IL | 0000239533 | 8/2015 |
| JP | H11-511178 | 9/1999 |
| JP | 2002-047158 | 2/2002 |
| JP | 2016519077 | 6/2016 |
| KR | 20030061874 | 7/2003 |
| KR | 20110103934 | 9/2011 |
| KR | 20130074422 | 7/2013 |
| RU | 2214225 | 10/2003 |
| RU | 2417070 | 4/2011 |
| RU | 2485941 | 6/2013 |
| RU | 2496716 | 10/2013 |
| RU | 2527693 | 9/2014 |
| RU | 2582945 | 4/2016 |
| TW | 200745267 | 12/2007 |
| WO | 1994/006868 | 3/1994 |
| WO | 1997/046485 | 12/1997 |
| WO | 2002/049588 | 6/2002 |
| WO | 2002/096221 | 12/2002 |
| WO | 2005/107456 | 11/2005 |
| WO | 2008/070368 | 6/2008 |
| WO | 2009/001697 | 12/2008 |
| WO | 2009/112458 | 9/2009 |
| WO | 2012/031785 | 3/2012 |
| WO | 2012/103037 | 8/2012 |
| WO | 2012/110995 | 8/2012 |
| WO | 2013/072852 | 5/2013 |
| WO | 2013/089759 | 6/2013 |
| WO | 2013/149323 | 10/2013 |
| WO | 2015/076817 | 5/2015 |
| WO | 2015/095606 | 6/2015 |
| WO | 2015/095608 | 6/2015 |
| WO | 2015/095704 | 6/2015 |
| WO | 2015/095709 | 6/2015 |
| WO | 2017/196299 | 11/2017 |
| WO | 2018/118911 | 6/2018 |

OTHER PUBLICATIONS

Alexei Smirnov. "Legal dispute over Holcomb intellectual property expands." The Nashville Post, https://www.nashvillepost.com/home/article/20448692/legal-dispute-over-holcomb-intellectual-property-expands downloaded Dec. 9, 2020, published Apr. 1, 2004, pp. 1-3. (Year: 2004).

Angelo C. Pinto et al. "Separation of Acid Diterpenes of Copalfera cearensis Huber ex Ducke by Flash Chromatography Using Potassium Hydroxide Impregnated Silica Gel." Journal of the Brazilian Chemical Society, vol. 11, No. 4, 2000, pp. 355-360. (Year: 2000).

Anna Torrado, Manuel Valiente, Carlos A. Munoz, "Cleaning power and abrasivity of a new toothpaste based on ion-exchange resins." American Journal of Dentislly, vol. 17, No. 2, Apr. 2004, pp. 80-84. (Year: 2004).

BYU Cleanroom. KOH Etching. https://cleanroom.byu.edu/KOH accessed Sep. 27, 2018, 20 printed pages. (Year: 2018).

Cardinal Search Report, Chemically Modified Si02 Practical in Dental Products, Supplemental Search, Nov. 5, 2013.

Cardinal Search Report, Chemically Modified Si02 Practical in Dental Products, Nov. 4, 2013.

CaseText. "*Holcomb Health Care Services, LLC* v. *Quart Limited, LLC* (In re Holcomb Health Care Services, LLC)." https://casetext.com/case/in-re-holcomb-health-care-services downloaded on Dec. 9, 2020, originally published Dec. 14, 2004, pp. 1-79. (Year: 2004).

Choksi et al., 2013, "A research review article on composite material," Asian Academy Research J. Multidiscip. 1(8):44-56.

Ciriminna et al., 2013, "The sol-gel route to advanced silica-based materials and recent applications" Chemical Reviews 113:6592-6620.

Zhuravlev, 2000, "The surface chemistry of amorphous silica. Zhuravlev model," Colloids and Surfaces: A: Physiochem. Eng. Aspects, 173:1-38.

English translation of CN 1695447 A. Patent originally published in Chinese on Nov. 16, 2005. Translation obtained by examiner on Jun. 13, 2017. 6 printed pages.

(56) References Cited

OTHER PUBLICATIONS

Fertani-Gmati et al., 2011, "Thermochemistry and kinetics of silica dissolution in NaOH aqueous solution," Thermochimica Acta, 513:43-48.

Gahlaut et al., 2013, "Evaluation of antibacterial potential of plant extracts using Resazurin based microtiter dilution assay," International Journal of Pharmacy and Pharmaceutical Sciences 5(2):372-376.

Greenberg, 1957, "The depolymerization of silica in sodium hydroxide Solutions," Journal of Physical Chemistry, 61(7):960-965.

International Search Report and the Written Opinion of the International Searching Authority in International Application No. PCT/US2017/065673, mailed Mar. 29, 2018.

International Search Report and Written Opinion of the International Searching Authority in International Application No. PCT/US2014/071298, mailed May 28, 2015.

International Search Report and Written Opinion of the International Searching Authority in International Application No. PCT/US2014/071304, mailed May 28, 2015.

International Search Report and Written Opinion of the International Searching Authority in International Application No. PCT/US2014/071502, mailed Apr. 22, 2015.

International Search Report and Written Opinion of the International Searching Authority in International Application No. PCT/US2014/071511, mailed Apr. 22, 2015.

International Search Report and Written Opinion of the International Searching Authority in International Application No. PCT/US2017/067296, mailed Mar. 23, 2018.

J Yamanaka, Y Hayashi, N Ise, T Yamaguchi. "Control of the surface charge density of colloidal silica by sodium hydroxide in salt-free and low-salt dispersions." Physical Review E, vol. 55 No. 3, Mar. 1997, pp. 3028-3036. (Year: 1997).

J. M. Rimsza, R. E. Jones, L. J. Criscenti, "Interaction of NaOH solutions with silica surfaces.", Journal of Colloid and Interface Science, vol. 516(2018), pp. 128-137. (Year:2018).

Kalele et al, "Nanoshell particles: synthesis, properties and applications", current science, vol. 91, No. 8, Oct. 25, 2006.

Lanlang Corporation, https://www.lanlangcorp.com/info/strong-base-anion-exchange-resin-example-41908792.html accessed Aug. 25, 2021, originally published Dec. 24, 2019, 5 printed pages. (Year: 2019).

Niibori et al., 2000, "Dissolution Rates of Amorphous Silica in Highly Alkaline Solution," Journal of Nuclear Science and Technology, 37(4):349-357.

Sten Ahrland, Ingmar Grenthe, and Bertil Noren. "The Ion Exchange Properties of Silica Gel, II. Separation of Plutonium and Fission Products from Irradiated Uranium." Acta Chemica Scandinavica, vol. 14, 1960, pp. 1077-1090. (Year: 1960).

Supelco, http://www.supelco.com.tw/B-11-Resins.pdf accessed Dec. 13, 2021, pp. 429-456. (Year: 2021).

Zhang et al., 2009, "Rattle-type silica colloidal particles prepared by a surface-protected etching process," Nano Research 2:583-591.

Berge et al., 1977, "Pharmaceutical Salts." Journal of Pharmaceutical Sciences, 66(1):1-19.

Evonik Operations GmbH. "Product Information Zeodent 115—For the sake of Clarity." Apr. 2021, pp. 1-2. (Year: 2021).

Evonik Resource Efficiency GmbH. "Product Information Zeodent 165." Dec. 2017, pp. 1-2 (Year: 2017).

Richard J.M. Lynch, 2011, "Zinc in the mouth, its interactions with dental enamel and possible effects on caries; a review of the literature. "International Dental Journal, 61 (Suppl 3):46-54.

CORE SHELL SILICA PARTICLES AND USE FOR MALODOR REDUCTION

BACKGROUND

Silica ($SiO_2$) particles are commonly used as abrasive and/or thickeners in oral care compositions usually in the form of fumed silica or precipitated silica. One of the benefits of using silica is their low cost. However, silica has limited utility besides its abrasive and/or thickening effect. As a result, other active agents must be added to an oral care composition to provide a desired effect (e.g., adding an anti-bacterial agent to provide an anti-bacterial effect, adding malodor-control agents for malodor control). The need to add other active agents not only raises the possibility that the oral care composition will not meet regulatory burdens which can arise when the other active agents are used, but also increases the possibility that the oral care composition will not be desirable to the user of the composition (e.g. user sensitivity to the surfactant sodium lauryl sulfate (SLS), user aversion to the taste of a zinc compound, salty flavor and crystallization issues with current tartar-control agents etc.). Moreover, further problems may arise. For example, a common problem with the use of an anti-bacterial agent is the development of resistance by bacteria to the agent.

Core-shell structured colloidal particles have been known for several decades. The most famous example is the light-diffracting precious Opal which is formed slowly in several thousand years in natural environments. Its core-shell structures were discovered by electron microscope in 1960s. Various synthetic core-shell colloidal particles have been made since then. However, the synthesis of such core-shell materials is often complex, requiring multistep coating methodologies (See Kalele et al, "Nanoshell particles: synthesis, properties and applications", current science, vol. 91, no. 8, 25 Oct. 2006). Therefore although the core-shell technology has been known for several decades, it has not yet been applied in the dentifrice industry, probably due to the high cost of making the CSS abrasive materials.

Therefore, there is still a need in the art for oral care compositions with multifunctional effects, but with a minimum of ingredients necessary to achieve the multifunctional effects. There is also still a need to develop additional anti-bacterial agents and malodor control agents suitable for use in oral care compositions.

Halitosis, (bad breath or oral malodor), is a common problem that can cause embarrassment and affect quality of life. Often people suffering from bad breath remain unaware of it. Oral malodor is produced by overgrowth of oral microorganisms that produce volatile sulfur compounds ("VSC") such as hydrogen sulphide, methylmercaptan and dimethyl sulphide. Treatment is aimed at the reduction of microorganisms in the oral cavity, neutralizing of the VSC compounds or masking the bad odors.

Adding anti-bacterial active agent or an active agent to neutralize the VSC compounds to an oral care composition to provide malodor-controlling effects raises the possibility that the oral care composition will not meet regulatory burdens which can arise when the other active agents are used, and also increases the possibility that the oral care composition will not be desirable to the user of the composition (e.g., due to zinc taste or expense of additional anti-bacterial agents). Being able to provide an anti-bacterial property to a component otherwise already included in oral-care compositions, such as an abrasive, thereby providing a multi-functional component, would be of great benefit.

It is well known that Zinc (Zn) can kill bacteria. Many pure Zn compounds have been tested in various formulations. The efficacy is controlled by two numbers: (1) total Zn and (2) soluble Zn2+. The biggest hurdle is the typical astringent taste coming from the Zn2+ ions which is the major factor to kill bacteria. So less soluble Zn compounds are favored.

Therefore, there is still a need in the art for oral care compositions with multifunctional effects, but with a minimum of ingredients necessary to achieve the multifunctional effects.

BRIEF SUMMARY

The present invention provides core shell silica particles, wherein each core shell silica particle comprises a silica core, and a surface of the silica core etched with a metal silicate, wherein the metal silicate is a silicate of:
i) a divalent metal ion, a trivalent metal ion, or a tetravalent metal ion, or;
ii) a monovalent metal ion and one or more of a of a divalent metal ion, a trivalent metal ion, and a tetravalent metal ion.

The present invention also provides core shell silica particles, wherein each core shell silica particle comprises a silica core, and a surface of the silica core etched with metal silicate, the core shell silica particles prepared by:
i) admixing an amount of silica particles in water with an amount of a base, wherein the base comprises a monovalent metal ion, to produce core shell silica particles, each core shell silica particle comprising a silica core, and a surface of the silica core etched with a silicate of the monovalent metal ion; and
ii) reacting the core shell silica particles formed in step i) with a metal salt comprising a second metal ion, to form core shell silica particles comprising silicate of the second metal ion on the surface of the silica core.

Core shell silica particles are prepared by etching silica ($SiO_2$) with a base to form core(Silica)-shell(metal silicate) structured colloids. For example using NaOH as the base, core($SiO_2$)-shell($Na_2SiO_3$) structured colloids are formed. The reaction is as follows:

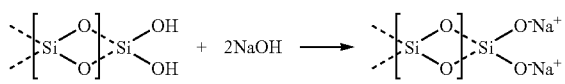

The $Na_2SiO_3$ molecules (contributing 2 negative charges with 2 Na+ counter ions) on colloidal core-shell silica particle surface are shown.

A surface of the silica core is etched with metal silicate. The term "etched" means that a surface of the silica core is dissolved, and metal silicate is formed on top of the silica core. The process for making the core shell silica particles comprises etching the original silica in order to form the metal silicate. The reaction of the silica particle with base causes a reduction in the diameter of the silica particle to form a silica core, and metal silicate is formed on top of the silica core. The metal silicate layers are not additional layers coated on top of the original surface of the silica. Methods of forming particles by coating silica with silicate are described in the prior art (e.g. Kalele et al, "Nanoshell particles: synthesis, properties and applications", current science, vol. 91, no. 8, 25 Oct. 2006). However, these methods of preparing silica/silicate particles are more complex and costly then the methods described in the present application.

The surface of the CSS particles formed in step i) has a high charge density and is strongly hydrophilic. Accordingly, in step ii) the core shell silica particles are complexed with a second metal ion, such as a zinc ion, wherein the second metal ion typically displaces the first metal ion from the surface of the CSS, e.g. zinc ions displace sodium ions.

In a further aspect, the present invention provides a process for making the core shell silica particles as defined above, the process comprising:
  i) admixing an amount of silica particles in water with an amount of a base, wherein the base comprises a first metal ion, to produce core shell silica particles, each core shell silica particle comprising a silica core, and a surface of the silica core etched with a silicate of the first metal ion; and
  ii) reacting the core shell silica particles formed in step i) with a metal salt comprising a second metal ion to form core shell silica particles comprising silicate of the second metal ion on a surface of the silica core.

CSS is prepared by etching silica with base comprising a first metal ion, such as NaOH, to form core($SiO_2$)-shell (metal silicate particles, such as core($SiO_2$)-shell($Na_2SiO_3$) particles. The silicate on the surface, such as $Na_2SiO_3$, can then react with a second metal ion, such as $Zn^{2+}$ to form novel CSS abrasives, such as core ($SiO_2$)-shell ($ZnSiO_3$) silica abrasives. By reacting metal ions such as zinc ions with the CSS, the amount of free, soluble metal ions is reduced. When the Zinc CSS particles are used in oral care compositions, the reduction in free zinc ions leads to an improvement in the taste profile of the oral care compositions, whilst at the same time achieving an antibacterial effect and a reduction in oral malodor of the user.

In an additional aspect, the present invention relates to a core shell silica particle obtainable by the process as defined above.

The present invention also relates to a method of reducing or eliminating malodor in the oral cavity of a patient in need thereof, which comprises applying to the oral surfaces of the patient an oral care composition comprising the core shell silica particles as defined above.

Another aspect of the invention is an oral care composition comprising the core shell silica particles as defined above for use in reducing or eliminating malodor in the oral cavity of a patient in need thereof, which use comprises applying to the oral surfaces of the patient the oral care composition.

As used throughout, ranges are used as shorthand for describing each and every value that is within the range, and for describing sub-ranges within the range. Any value within the range can be selected as the upper terminus of the sub-range. Any value within the range can be selected as the lower terminus of the sub-range.

In addition, all references, books, patents, and patent application publications cited herein are hereby incorporated by reference in their entireties. In the event of a conflict in a definition in the present disclosure and that of a cited reference, book, patent, or patent application publication, the present disclosure controls.

Unless otherwise specified, reference to ambient or room temperature refers to a temperature range of 20-25° C.

Reference to Group I metal CSS particles refer to the metal with the appropriate +1 charge for the metal, e.g. for Na-CSS, the Na is Na+, for K-CSS, the K is K+. Reference to metal CSS particles with a charge of 2+ or greater is referenced as M-CSS (e.g. Zn-CSS or Ca-CSS), this designation also includes any remaining Group I metal on the outer surface of the CSS particle (e.g. a Na-CSS particle synthesized to make Zn-CSS may also include Na+ on the outer surface as well as $Zn^{2+}$; may also be designated generically as Group I metal-M-CSS (e.g. Na—Zn-CSS).

Unless otherwise specified, all percentages and amounts expressed herein and elsewhere in the specification should be understood to refer to percentages by weight based on the total weight of the composition.

The phrase "and/or" as used herein, with option A and/or option B for example, encompasses the individual embodiments of (i) option A; (ii) option B; and (iii) option A plus option B.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group and all possible subgroups of the main group, but also the main group absent one or more of the group members. The present invention also envisages the explicit exclusion of one or more of any of the group members in the claimed invention.

All combinations of the various elements described herein are within the scope of the invention unless otherwise indicated herein or otherwise clearly contradicted by context.

Further areas of applicability of the present invention will become apparent from the detailed description provided hereinafter. It should be understood that the detailed description and specific examples are intended for purposes of illustration only and are not intended to limit the scope of the invention.

DETAILED DESCRIPTION

Figure 1:
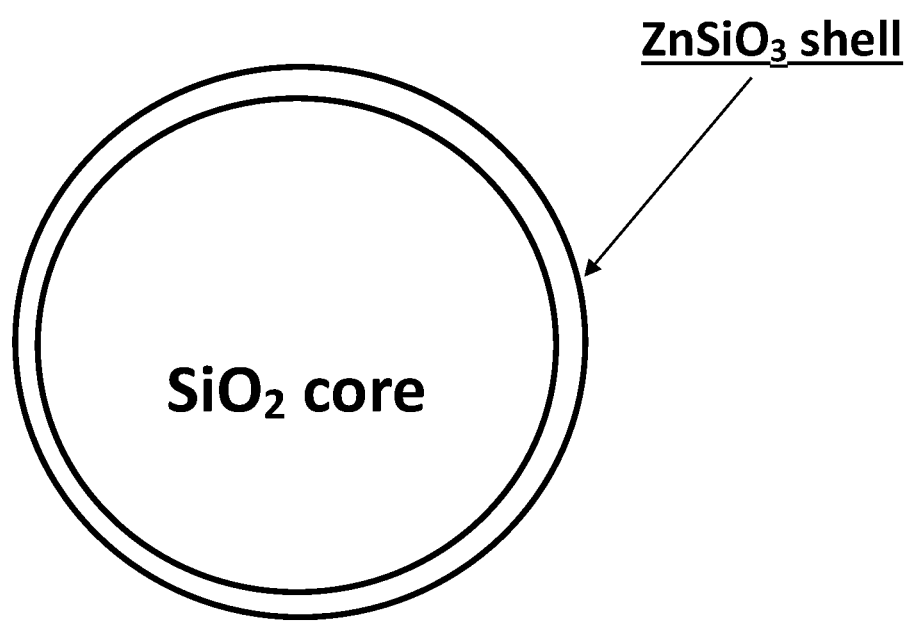
FIG. 1 shows a schematic of a core shell silica particle according to the present invention.
Figure 2:
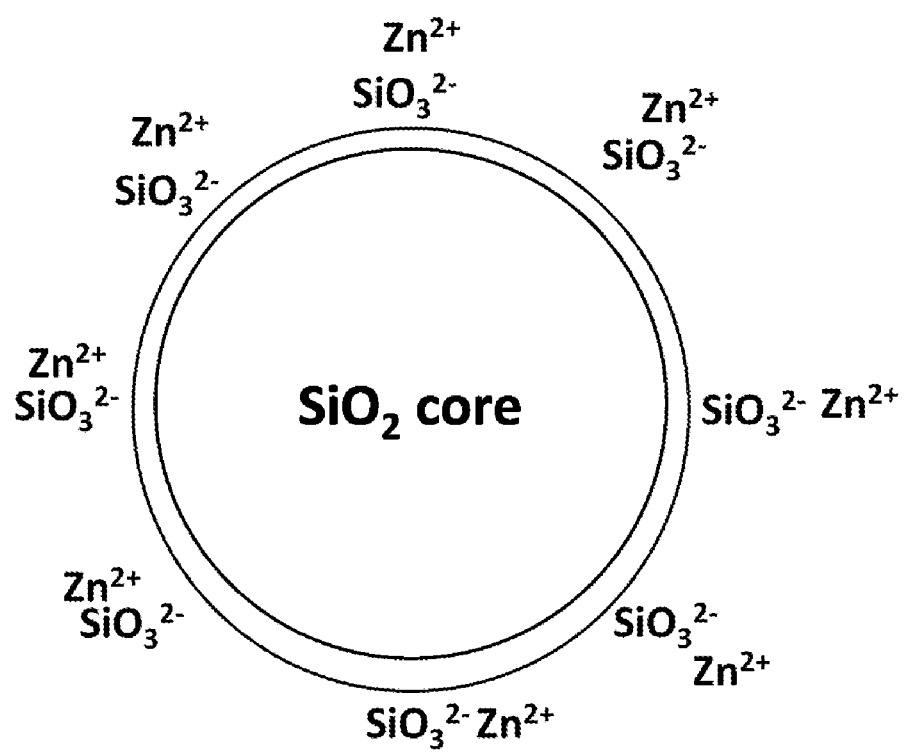
FIG. 2 shows a schematic of a core shell silica particle wherein metal silicate is etched on an inner surface of a silica core.

The following description of the preferred embodiment(s) is merely exemplary in nature and is in no way intended to limit the invention, its application, or uses.

Description of the Core Shell Silica Particles

The present invention provides core shell silica particles, wherein each core shell silica particle comprises a silica core, and a surface of the silica core etched with a metal silicate, wherein the metal silicate is a silicate of:
  i) a divalent metal ion, a trivalent metal ion, or a tetravalent metal ion, or;
  ii) a monovalent metal ion and one or more of a of a divalent metal ion, a trivalent metal ion, and a tetravalent metal ion.

Typically, the metal silicate comprises a silicate of a group 2 metal ion, a transition metal ion, a group 13 metal ion, a group 14 metal ion or mixtures thereof. Optionally, the metal silicate comprises a silicate of $Ca^{2+}$, $Mg^{2+}$, $Zn^{2+}$, $Sn^{2+}$, $Sr^{2+}$, $Al^{3+}$, $Zr^{4+}$, $Ti^{4+}$, $Fe^{3+}$, $Fe^{2+}$, $Mo^{2+}$, $Co^{2+}$, $Ni^{2+}$, $Mn^{2+}$, $Cu^{2+}$, $Pd^{2+}$, $Mo^{2+}$, $Ru^{2+}$ or mixtures thereof.

The metal silicate may comprise a monovalent ion and one or more of a divalent metal ion, a trivalent metal ion, and a tetravalent metal ion. These types of CSS particles are typically formed when the monovalent ions are not completely substituted for divalent, trivalent or tetravalent ions. The monovalent ion may be selected from $Na^+$ or $K^+$.

Optionally the metal silicate comprises the formula $M^2SiO_3 \cdot x\, H_2O$, wherein $M^2$ is a divalent metal ion, and x is from 0 to 10. $M^2$ may be selected from the group consisting of Zn, Ca, Mg, Sn, and Sr, optionally wherein $M^2$ is Zn.

The present invention also provides core shell silica particles, wherein each core shell silica particle comprises a silica core, and a surface of the silica core etched with metal silicate, the core shell silica particles prepared by:
  i) admixing an amount of silica particles in water with an amount of a base, wherein the base comprises a monovalent metal ion, to produce core shell silica particles, each core shell silica particle comprising a silica core, and a surface of the silica core etched with a silicate of the monovalent metal ion; and
  ii) reacting the core shell silica particles formed in step i) with a metal salt comprising a second metal ion, to form core shell silica particles comprising silicate of the second metal ion on the surface of the silica core.

It will be understood that the second metal ion typically displaces the monovalent metal ion from the metal silicate on the surface of the silica core. The monovalent metal ion and second metal ion may be present in the silicate in a weight ratio of 1:1, 1:2, 1:3, or 1:4 monovalent:second metal ion in the final CSS product of the process. In another embodiment substantially all of the monovalent metal ion is displaced.

In a preferred embodiment the monovalent metal ion is a group 1 metal ion. Particularly preferred as the monovalent metal ion is a sodium ion or potassium ion.

The base is not especially limited, provided it comprises the monovalent metal ion. The base is typically a strong base. The base may be selected from the group consisting of sodium hydroxide, potassium hydroxide, sodium carbonate, potassium carbonate, trisodium phosphate, disodium phosphate, potassium phosphate, dipotassium phosphate, tetrasodium pyrophosphate, and tetrapotassium pyrophosphate. Sodium or potassium hydroxide are preferred bases. The base may have a pKb value in the range 0.1 to 3. For example sodium hydroxide has a pKb of 0.2, and potassium hydroxide has a pKb of 0.5.

The second metal ion is not especially limited provided it can displace the monovalent metal ion from the silicate of the monovalent metal ion. The second metal ion may be a divalent metal ion, a trivalent metal ion, a tetravalent metal ion or mixtures thereof. Most preferably the second metal ion is a divalent metal ion. The second metal ion may be a group 2 metal ion, a transition metal ion, a group 13 metal ion, a group 14 metal ion or mixtures thereof. Preferably the second metal ion is $Ca^{2+}$, $Mg^{2+}$, $Zn^{2+}$, $Sn^{2+}$, $Sr^{2+}$, $Al^{3+}$, $Zr^{4+}$, $Ti^{4+}$, $Fe^{3+}$, $Fe^{2+}$, $Mo^{2+}$, $Co^{2+}$, $Ni^{2+}$, $Mn^{2+}$, $Cu^{2+}$, $Pd^{2+}$, $Mo^{2+}$, $Ru^{2+}$ or mixtures thereof. In a particularly preferred embodiment the second metal ion is $Zn^{2+}$.

By changing the monovalent and second metal ions, core shell silica particles with different utilities can be provided. For example Zn-CSS are useful as antibacterial agents and anti-malodor agents, with a taste profile which is better than the taste profile of zinc salts such as $ZnCl_2$. The silicates may be hydrated or anhydrous.

In one embodiment the silicate of the monovalent metal ion formed in step i) comprises the formula $M^1{}_2SiO_3 \cdot x\, H_2O$, wherein $M^1$ is a monovalent metal ion, optionally a group I metal ion, and x is from 0 to 10. $M^1$ is preferably $Na^+$ or $K^+$.

The silicate of the second metal ion formed in step ii) typically comprises the formula $M^2SiO_3 \cdot x\, H_2O$, wherein $M^2$ is a divalent metal ion, and x is from 0 to 10. $M^2$ is preferably selected from the group consisting of $Zn^{2+}$, $Ca^{2+}$, $Mg^{2+}$, $Sn^{2+}$, and $Sr^{2+}$.

The silica is preferably selected from the group consisting of a precipitated silica, a fumed silica and a fused silica.

Fumed Silica

Pyrogenic silica (sometimes called fumed silica or silica fume) is a very fine particulate or colloidal form of silicon dioxide. It is prepared by burning $SiCl_4$ in an oxygen rich hydrocarbon flame to produce a "smoke" of $SiO_2$. The silica particles fuse with one another to form branched, three-dimensional chain-like aggregates.

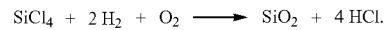

$$SiCl_4 + 2\,H_2 + O_2 \longrightarrow SiO_2 + 4\,HCl.$$

Precipitated Silica

Amorphous silica, silica gel, is produced by the acidification of solutions of sodium silicate. An initially formed gelatinous precipitate is then washed and then dehydrated to produce colorless microporous silica. Idealized equation involving a trisilicate and sulfuric acid is shown:

$$Na_2Si_3O_7 + H_2SO_4 \longrightarrow 3\,SiO_2 + Na_2SO_4 + H_2O$$

In the majority of silicates, the Si atom shows tetrahedral coordination, with 4 oxygen atoms surrounding a central Si atom. The most common example is seen in the quartz crystalline form of silica $SiO_2$. In each of the most thermodynamically stable crystalline forms of silica, on average, all 4 of the vertices (or oxygen atoms) of the $SiO_4$ tetrahedra are shared with others, yielding the net chemical formula: $SiO_2$. $SiO_2$ has a number of distinct crystalline forms (polymorphs) in addition to amorphous forms. With the exception of stishovite and fibrous silica, all of the crystalline forms involve tetrahedral $SiO_4$ units linked together by shared vertices in different arrangements.

Sodium Silicate

Sodium silicate is the common name for compounds with the formula $Na_2(SiO_2)_nO$. A well-known member of this series is sodium metasilicate, $Na_2SiO_3$. Also known as waterglass or liquid glass, these materials are available in aqueous solution and in solid form. Sodium carbonate and silicon dioxide react when molten to form sodium silicate and carbon dioxide:

$$Na_2CO_3 + SiO_2 \longrightarrow Na_2SiO_3 + CO_2$$

Anhydrous sodium silicate contains a chain polymeric anion composed of corner shared $\{SiO_4\}$ tetrahedral, and not a discrete $SiO_3{}^{2-}$ ion. In addition to the anhydrous form, there are hydrates with the formula $Na_2SiO_3 \cdot nH_2O$ (where n=5, 6, 8, 9) which contain the discrete, approximately tetrahedral anion $SiO_2(OH)_2^{2-}$ with water of hydration. For example, the commercially available sodium silicate pentahydrate $Na_2SiO_3 \cdot 5H_2O$ is formulated as $Na_2SiO_2(OH)_2 \cdot 4H_2O$ and the nonahydrate $Na_2SiO_3 \cdot 9H_2O$ is formulated as $Na_2SiO_2(OH)_2 \cdot 8H_2O$.

In industry, the various grades of sodium silicate are characterized by their $SiO_2:Na_2O$ weight ratio (weight ratios can be converted to molar ratios by multiplication with 1.032), which can vary between 2:1 and 3.75:1. Grades with this ratio below 2.85:1 are termed 'alkaline'. Those with a higher $SiO_2:Na_2O$ ratio are described as 'neutral'.

Precipitated silica includes, but is not limited to Zeodent® 114 and Zeodent® 165 (precipitated silica particles produced by J.M. Huber—synthetic amorphous silica), Sylodent® 783 produced by W.R. Grace, Sorbosil® AC-43 produced by Ineos (PQ Corp.)

The silica may be a fumed silica, such as Aerosil 200, produced by Evonik.

In another embodiment, the silica is a fused silica, which includes but is not limited to CAB-O-SIL® HP-60, produced by Cabot Corporation, TECO-SIL® 10 and TECO-SIL® 44css, produced by C-E Minerals, and Spheron P1500 made by the Japanese Glass Co.

Core shell silica particles of the invention typically comprise a plurality of monolayers of metal silicate. The number of monolayers may be from 2 to 100, 2 to 40, 2 to 12 or 12 to 40 layers. The particle may comprise 2, 4, 16, 32 or 36 monolayers.

The metal salt may be selected from the group consisting of a metal acetate, metal borate, metal butyrate, metal carbonate, metal halide, metal citrate, metal formate, metal gluconate, metal glycerate, metal glycolate, metal lactate, metal oxide, metal phosphate, metal picolinate, metal proprionate, metal salicylate, metal silicate, metal stearate, metal tartrate, metal undecylenate and mixtures thereof. In a preferred embodiment the metal salt is a metal halide. Most preferably, the metal halide is a metal chloride. Examples are $ZnCl_2$, $SnCl_2$, $SrCl_2$, $AlCl_3$, $FeCl_3$, $TiCl_4$, and $ZrCl_4$. In a particularly preferred embodiment the metal salt is a zinc salt. The metal salt may be a zinc salt selected from the group consisting of zinc acetate, zinc borate, zinc butyrate, zinc carbonate, zinc chloride, zinc citrate, zinc formate, zinc gluconate, zinc glycerate, zinc glycolate, zinc lactate, zinc oxide, zinc phosphate, zinc picolinate, zinc proprionate, zinc salicylate, zinc silicate, zinc stearate, zinc tartrate, zinc undecylenate and mixtures thereof. The most preferred zinc salt is zinc chloride.

In a preferred embodiment the silicate of the second metal ion comprises $ZnSiO_3 \cdot xH_2O$, wherein x is from 0 to 10.

In one embodiment the surface of the silica core is the outer surface of the silica core. In addition or as an alternative the surface of the silica core may be an internal surface of the silica core.

The silicate of the second metal ion may comprise at least 30 weight %, 40 weight % 50 weight % 60 weight %, 70 weight %, 80 weight % or 90 weight % of the total metal silicate of the CSS particles. Preferably, the silicate of the second metal ion comprises at least 90 weight % of the total metal silicate of the CSS particles.

The outer 10 nm depth of each particle may comprise from 0.1 to 10 weight % metal silicate. In one embodiment the outer 10 nm depth of each particle has the general formula:

$$(SiO_2)_p[O^*_o N_n^+ M_m^{2+} U_u^{3+} V_v^{4+} H_h^+] \cdot qH_2O$$

wherein O* is oxygen in the silicate form; N is a monovalent metal ion; M is a divalent metal ion; U is a trivalent metal ion; V is a tetravalent metal ion; p, o, n, m, u, v, h and q are the atomic percentages of each component; and the total charge of each core shell silica particle is zero.

The atomic percentage for each component except H+ is typically determined by electron spectroscopy for chemical analysis (ESCA). In one example, using ESCA data, the following elements were detected:

$$O_{56.81}Si_{26.52}O^*_{7.35}Na_{3.18}Zn_{4.65}Cl_{1.49}$$

By setting the total electric charge to zero by adding H+ and water, we conclude that in one embodiment the outer 10 nm depth of each particle may have the following composition:

$$(SiO_2)_{26.52}[O^*_{7.35}Na_{3.18}Zn_{4.65}Cl_{1.49}H_{3.73}] \cdot 3.77H_2O$$

The d(0.5) value of the particles is typically from 5 nm to 50 μm.

The d(0.5) value of the particles may be from 26 μm to 40 μm. Particles having a d(0.5) value within this range are typically opaque. Translucent particles are those which allow light to pass through, although it is not possible to see an image through the particles. This is distinguished from transparent compositions which allow light to pass through and an image can be seen through the composition. Methods for determining particle size are well known in the art. For example particle size may be determined using light scattering methodologies, such as using the Mastersizer 2000, Hydro 20005, Malvern Instruments Limited.

The d(0.5) value of the particles may be from 18 μm to 25 μm. Particles having a d(0.5) value within this range are typically opaque.

The d(0.5) value of the particles may be from 10 μm to 15 μm. Particles having a d(0.5) value within this range are typically opaque.

In another embodiment, the d(0.5) value of the CSS particles may be from 5 μm to 15 μm.

In another embodiment, the d(0.5) value of the CSS particles may be from 2.5 μm to 4.5 μm.

In another embodiment, the d(0.5) value of the CSS particles may be from 5 nm to 20 nm.

In another embodiment, the d(0.5) value of the CSS particles may be from 10 nm to 15 nm.

In another embodiment, the d(0.5) value of the particles may be from 5 nm to 12 nm.

The d(0.5) or d50 of the particles is the diameter (typically in microns) that splits the distribution with half the population above and half below this diameter. The Dv50 (or Dv0.5) is the median for a volume distribution, Dn50 is used for number distributions, and Ds50 is used for surface distributions. In the present context, d(0.5) will be used to refer to the median particle size for a volume distribution (Dv0.5).

The d(0.1) value of the particles is the diameter that splits the distribution with 10% of the population below and 90% above this diameter.

The d(0.9) value of the particles is the diameter that splits the distribution with 90% of the population below and 10% above this diameter.

A value used to describe the distribution width of the particle size distribution is the span: Span=(d(0.9)−d(0.1))/d(0.5)

The span of the core shell silica particles according to the present invention is typically from 1.5 to 3.

In a preferred embodiment, the CSS have a d(0.1) of from 10 to 13 μm, a d(0.5) of from 30 to 33 μm, and a d(0.9) of from 61 to 64 μm.

In another preferred embodiment, the CSS have a d(0.1) of from 6 to 9 μm, a d(0.5) of from 18 to 21 μm, and a d(0.9) of from 41 to 45 μm.

In a further preferred embodiment, the CSS have a d(0.1) of from 3 to 5 μm, a d(0.5) of from 11 to 14 μm, and a d(0.9) of from 33 to 36 μm.

In preferred embodiments, the d(0.5) value of the CSS particles is less than the mean diameter of a human dentin tubule. This allows the CSS particles to enter the dentin tubules, which may be exposed on damage to the protective enamel layer. In human teeth, dentin tubule mean diameter near the dentino-enamel junction is 0.9 m, the middle section of the dentin tubule has a diameter of about 1.2 m and near the pulp the diameter is about 2.5 m.

In another embodiment of the invention, a silica source is selected to produce CSS particles which fits into the dentin tubule (e.g. Aerosil® 200—a fumed silica (synthetic amorphous silica) with a d(0.5) of 0.012 m). In another embodiment of the invention, the d(0.5) value of the CSS particles is less than 0.9 m. In still another embodiment of the invention, the CSS particle has a d(0.5) in the range of 0.010 m-less than 0.9 m. In another embodiment of the invention, the CSS particles of the invention can also plug, block holes in the enamel.

The core shell silica particles may comprise up to 20 weight % total metal, preferably zinc.

The present core shell silica particles have surprisingly high surface charge density and ion exchange capacity.

In an embodiment, the core shell silica particles have a surface charge density of from 0.5 to 4.5 meq/g silica. In an embodiment, the core shell silica particles have surface charge density of from 2 to 3 meq/g silica. In an embodiment, the core shell silica particles have a surface charge density of 2.45-2.55 meq/g silica.

In an embodiment, the core shell silica particles have a charge, or ion-exchange capacity of, from 0.05 to 0.1 C/cm$^2$ surface area. In an embodiment, the core shell silica particles have a charge, or ion-exchange capacity, of from 0.085 to 0.095 C/cm$^2$ surface area. In an embodiment, the core shell silica particles have a charge, or ion-exchange capacity, of from 0.089 C/cm$^2$ surface area.

In an embodiment of Zn-CSS particles, the amount of zinc adsorbed to surface monolayers of the particles is less than 50% of the maximum ion-exchange capacity of the particle for divalent ions. In an embodiment, the amount of zinc adsorbed to surface monolayers of the particles is 30-35% of the maximum ion-exchange capacity of the particle for divalent ions. In an embodiment, the amount of zinc adsorbed to surface monolayers of the particles is 33% of the maximum ion-exchange capacity of the particle for divalent ions.

Compositions Comprising Core Shell Silica Particles

In a further aspect, the present invention provides a composition comprising the core shell silica particles as defined above.

In one embodiment the composition comprises from 0.0 to 0.5 weight % soluble metal ions. The soluble metal ions may be zinc ions. One of the advantages of the CSS compositions of the present invention is that CSS particles complex with metal ions such that the concentration of free metal ions in solution is low. High concentrations of free metal ions, such as zinc ions can provide disadvantages, particularly for oral care compositions. For example, a high concentration of soluble zinc ions can lead to a poor taste profile for the composition.

In one embodiment the composition is a powder abrasive. Powder abrasive compositions do not comprise humectants.

The composition may comprise the core shell silica particles as defined above and a carrier. In a preferred embodiment the composition is an oral care composition and further comprises an orally acceptable carrier. For oral care compositions the second metal ion is preferably zinc. As described above, and in further detail in the Examples below, Zn-CSS provide anti-bacterial and anti-malodor effects, and an improved taste profile over Zinc salts such as $ZnCl_2$.

In an embodiment of the composition, the core shell silica particles comprise a range selected from the ranges consisting of 0.1% to 35 weight %, based on the weight of the composition. In another embodiment of the composition, the CSS particles are present in an amount from 0.1% to 1%. In another embodiment of the composition, the CSS particles are present in an amount from 0.5% wt. % to 20 wt. %, In another embodiment of the composition, the CSS particles are present in an amount from 1% wt. % to 10 wt. %.

In an embodiment, the metal salt is present at 0.01-3.0 weight % of the composition. In an embodiment, the metal salt is present at 0.01-1.5 weight % of the composition. In an embodiment, the metal salt is present at 0.01-1.0 weight %. In an embodiment, the metal salt is present at 0.1-0.5 weight %. In an embodiment, the metal salt is present at 0.1%. In an embodiment, the metal salt is present at 1 weight % or 2 weight %. In an embodiment the metal salt is $ZnCl_2$ in an amount of from 0.5% to 2 weight % of the composition.

In another embodiment of the invention, the composition may take any dosage form useful for oral administration. In an embodiment, the composition is a solid, a paste, a gel, or a liquid.

Illustrative examples of these include, but are not limited to, a dentifrice, e.g., a toothpaste, dental gel, dental cream, or tooth powder; a mouthwash, mouth rinse, or mouth spray; an oral slurry or liquid dentifrice; a gum or other confectionary; a lozenge; dental floss or dental tape; a prophylaxis paste or powder; a mono- or multi-layer oral film or gel strip, e.g., tooth strips or breath strips, preferably using a biodegradable or orally consumable film or gel; functional film or gel flakes or functional milli-, micro-, or nano-particles; a film-forming composition comprising pre-gel(s) or pre-polymer(s), e.g., film-forming dentifrices, dental paints; a tooth hardener; or a coating on an oral, e.g., orthodontic, appliance or implant.

For solid dentifrices such as toothpastes, the amount of water in the composition is selected from an amount consisting of less than 10% by weight, less than 5% by weight, less than 1% by weight. In each of these amounts, the lower range for the amount of water is 0% or no more than 0.1% water.

In an embodiment of an oral care composition, the composition further comprises an additional anti-malodor agent. In an embodiment, the additional anti-malodor compound is a known odor-controlling agent. In addition, other metal-containing compounds, such as those of copper, stannous, bismuth, strontium; and succulents or other ingredients which increase salivary flow, act to wash away odors, are useful in the compositions described herein. Certain strong citrus-based flavorants, odor-absorption complexes, which entrap or adsorb malodor molecules are also useful in the claimed compositions. For example, Ordenone® has the ability to encapsulate malodor molecules such as mercaptans, sulfides and amines within its structure, as disclosed in, for example, U.S. Pat. No. 6,664,254. Odor-controlling actives suitable also include, but are not limited to, enzymes that can interrupt the process by which odors are created. For example, odor-blocking enzymes such as arginine deiminase, can be effectively formulated in the compositions of the invention. Also, molecules that effectively inhibit the bacterial production of malodor molecules can be used to control odor, for example agents that interfere with the bacterial enzymes cysteine desulfhydrase and/or methionine gamma-lyase. Odor-controlling actives suitable for odor blocking or as odor blockers, include but are not limited to agents that act by oxidizing or otherwise chemically reacting with malodor molecules, including peroxides, perchlorites, and reactive molecules with activated double bonds.

In another embodiment of the oral care composition, there is no additional anti-malodor agent except for the core shell silica particles of the invention.

In an embodiment of the composition comprising a carrier, the refractive index of the core shell silica particles is within ±0.1 units of the refractive index of the carrier.

The carrier may include, but is not limited to water or other aqueous solvent systems.

The orally acceptable carrier may further comprise a humectant. Possible humectants are ethanol, a polyhydric alcohol, which includes, but is not limited to glycerin, glycol, inositol, maltitol, mannitol, sorbitol, xylitol, propylene glycol, polypropylene glycol (PPG), polyethylene glycol (PEG) and mixtures thereof, or a saccharide, which includes, but is not limited to fructose, glucose, sucrose and mixtures of saccharides (e.g. honey).

The oral care composition may further comprise an anti-bacterial agent, which is not the core shell silica particle of the invention. The anti-bacterial agent may be triclosan (5-chloro-2-(2,4-dichlorophenoxy)phenol); 8-hydroxyquinoline and salts thereof, zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride,); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; magnolia extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; or mixtures thereof.

In some embodiments, the anti-bacterial agent is present at a concentration selected from the group consisting of from 0.001% to 3%, by weight, 0.05% to 2%, by weight and 0.075% to 1.5% by weight.

Alternatively, there is no additional anti-bacterial agent except for the core shell silica particles of the invention.

In one embodiment the oral care composition further comprises a source of soluble metal ions. The soluble metal ions may be soluble zinc ions, such as $ZnCl_2$. For example CSS particles may be treated to remove soluble metal ions, and then a source of soluble metal ions is subsequently added to the composition such that the concentration of soluble metal ions is controlled.

The composition may further include anti-caries agents, desensitizing agents, viscosity modifiers, diluents, surfactants, emulsifiers, foam modulators, pH modifying agents, abrasives, mouth feel agents, sweetening agents, flavor agents, colorants, preservatives, amino acids, anti-oxidants. anti-calculus agents, a source of fluoride ions, thickeners, an active agent for prevention or treatment of a condition or disorder of hard or soft tissue of the oral cavity, adhesive agents, a whitening agent and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

An embodiment of the composition optionally comprises an amino acid. Suitable amino acids include, but are not limited to arginine, cysteine, leucine, isoleucine, lysine, alanine, asparagine, aspartate, phenylalanine, glutamate, glutamic acid, threonine, glutamine, tryptophan, glycine, valine, praline, serine, tyrosine, and histidine, and a combination of two or more thereof. The amino acids can include R- and L-forms and salt forms thereof. The amino acids (and salt forms thereof) can also include acid ester and/or fatty amide derivatives of the amino acid (e.g. ethyl lauroyl arginate hydrochloride (ELAH)).

An embodiment of the composition optionally comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

An embodiment of the composition optionally comprises an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The anticalculus agent is present at about 0.1% to about 30%. The oral composition may include a mixture of different anticalculus agents. In one preferred embodiment, tetrasodium pyrophosphate (TSPP) and sodium tripolyphosphate (STPP) are used. The anticalculus agent comprises TSPP at about 1-2% and STPP at about 7% to about 10%.

An embodiment of the composition optionally comprises at least one orally acceptable source of fluoride ions. Any known or to be developed in the art may be used. Suitable sources of fluoride ions include fluoride, stannous fluoride, sodium fluoride, potassium fluoride, amine fluoride, ammonium fluoride, stannous monofluorophosphate, sodium monofluorophosphate, potassium monofluorophosphate, amine monofluorophosphate, ammonium monofluorophosphate, stannous fluorosilicate, sodium fluorosilicate, potassium fluorosilicate, amine fluorosilicate ammonium fluorosilicate, and mixtures thereof. One or more fluoride ion-releasing compound is optionally present in an amount providing a total of about 100 to about 20,000 ppm, about 200 to about 5,000 ppm, or about 500 to about 2,500 ppm, fluoride ions.

An embodiment of the composition optionally comprises various dentifrice ingredients to adjust the rheology and feel of the composition such as surface active agents, thickening or gelling agents, etc.

An embodiment of the composition optionally comprises a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

An embodiment of the composition optionally comprises a surface active agent (surfactant). Suitable surfactants include without limitation water-soluble salts of $C_8$-$C_{20}$ alkyl sulfates, sulfonated monoglycerides of $C_8$-$C_{20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

An embodiment of the composition optionally comprises a thickener. Any orally acceptable thickening agent can be used, including without limitation carbomers, also known as carboxyvinyl polymers, carrageenans, also known as Irish moss and more particularly—carrageenan (iota-carrageenan), high molecular weight polyethylene glycols (such as Carbowax®., available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

An embodiment of the composition optionally comprises flavorants, sweeteners, colorants, foam modulators, mouthfeel agents and others additively may be included if desired, in the composition.

An embodiment of the composition optionally comprises one or more further active material(s), which is operable for the prevention or treatment of a condition or disorder of hard or soft tissue of the oral cavity, the prevention or treatment of a physiological disorder or condition, or to provide a cosmetic benefit. Examples of such further active ingredient comprise a sialagogue or saliva-stimulating agent, an antiplaque agent, an anti-inflammatory agent, and/or a desensitizing agent.

Adhesion enhancing agents can also be added to the oral care compositions which include but is not limited to waxes, inclusive of bees' wax, mineral oil, plastigel, (a blend of mineral oil and polyethylene), petrolatum, white petrolatum, shellac, versagel (blend of liquid paraffin, butene/ethylene/styrene hydrogenated copolymer) polyethylene waxes, microcrystalline waxes, polyisobutene, polyvinyl pyrrolidone/vinyl acetate copolymers, and insoluble polyacrylate copolymers.

Also effective as adhesion enhancing agents are liquid hydrophilic polymers including polyethylene glycols, nonionic polymers of ethylene oxide having the general formula: $HOCH_2(CH_2OCH_2)_{n1}CH_2OH$ wherein n1 represents the average number of oxyethylene groups. Polyethylene glycols available from Dow Chemical are designated by a number such as 200, 300, 400, 600, 2000 which represents the approximate average molecular weight of the polymer, as well as nonionic block copolymer of ethylene oxide and propylene oxide of the formula: $HO(C_2H_4O)_{a1}(C_3H_6O)_{b1}(C_2H_4O)_{c1}H$. The block copolymer is preferably chosen (with respect to a1, b1 and c1) such that the ethylene oxide constituent comprises from about 65 to about 75% by weight, of the copolymer molecule and the copolymer has an average molecular weight of from about 2,000 to about 15,000 with the copolymer being present in the liquid tooth whitening composition in such concentration that the composition is liquid at room temperatures.

A particularly desirable block copolymer for use in the practice of the present invention is available commercially from BASF and designated Pluraflo L1220 (PEG/PPG 116/66) which has an average molecular weight of about 9,800. The hydrophilic poly(ethylene oxide) block averages about 65% by weight of the polymer.

Synthetic anionic polycarboxylates may also be used in the oral compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000 most preferably about 30,000 to about 700,000. Examples of these copolymers are available from GAF Corporation under the trade name GANTREZ® (methylvinylether/maleic anhydride), e.g., AN 139 (M.W. 500,000), AN 119 (M.W. 250,000); S-97 Pharmaceutical Grade (M.W. 700,000), AN 169 (M.W. 1,200,000-1,800,000), and AN 179 (M.W. above 1,800,000); wherein the preferred copolymer is S-97 Pharmaceutical Grade (M.W. 700,000).

When present, the anionic polycarboxylates is employed in amounts effective to achieve the desired enhancement of the efficacy of any antibacterial, antitartar or other active agent within the oral composition. Generally, the anionic polycarboxylates is present within the oral composition from about 0.05% to about 4% by weight, preferably from about 0.5% to about 2.5% by weight.

Adhesion enhancing agents employed in compositions of various embodiments of the invention are present in an amount of from about 0 to about 20% by weight. Preferably, the adhesion enhancing agents are present in an amount of from about 2 to about 15% by weight.

An embodiment of the composition optionally comprises a whitening agent which includes, but is not limited to peroxide compounds such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof.

In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite, pigments or dyes. In some embodiments the whitening agent is separated from the aqueous carrier. In some embodiments the whitening agent is separated from the aqueous carrier by encapsulation of the whitening agent.

In one embodiment of the composition, the composition comprises about 65%-99.9% of the carrier and further included ingredients, i.e. one or more of anti-caries agents, desensitizing agents, viscosity modifiers, diluents, surfactants, emulsifiers, foam modulators, pH modifying agents, abrasives, mouth feel agents, sweetening agents, flavor agents, colorants, preservatives, amino acids, anti-oxidants, anti-calculus agents, a source of fluoride ions, thickeners, an active agent for prevention or treatment of a condition or disorder of hard or soft tissue of the oral cavity, a whitening agent and combinations thereof. In another embodiment of the composition, the composition comprises about 80%-99.5% of the carrier and further included ingredients. In another embodiment of the composition, the composition comprises about 90%-99% of the carrier and further included ingredients.

The description of the optional ingredients above is also intended to include any combination of ingredients.

Process of Making the Core Shell Silica Particles

In an additional aspect, the present invention provides a process for making the core shell silica particles as defined above, the process comprising:
i) admixing an amount of silica particles in water with an amount of a base, wherein the base comprises a first metal ion, to produce core shell silica particles, each core shell silica particle comprising a silica core, and a surface of the silica core etched with a silicate of the first metal ion; and
ii) reacting the core shell silica particles formed in step i) with a metal salt comprising a second metal ion to form core shell silica particles comprising silicate of the second metal ion on a surface of the silica core.

Step i) of the invention may comprise admixing an amount of $SiO_2$ particles in water with an amount of NaOH in solid or aqueous form, with or without a humectant, to produce the core shell silica particle. Sodium hydroxide reacts with the surface of the $SiO_2$ particle to etch a shell of layers(s) of $Na_2SiO_3$ as follows:

$$SiO_2 + 2\,NaOH \longrightarrow Na_2SiO_3 + H_2O$$

As can be seen from the reaction scheme, no NaOH will result in no change to the silica, whereas at the other extreme, complete reaction with 2 moles of NaOH per 1 mole of silica will result in the complete conversion into $Na_2SiO_3$. In order, to obtain the core shell particles of the invention, the reaction process must be controlled so as to not achieve complete conversion into $Na_2SiO_3$.

The process for making the core shell silica particles comprises of etching the original silica in order to form metal silicate layers, i.e. the metal silicate layers are not additional layers coated on top of the surface of the silica.

As the covalent bonds of the $SiO_2$ network are turned into ionic bonds between $Na^+$ and $SiO_3^{2-}$, the surface becomes polarized and adsorbs water and the humectant to produce the core shell silica particle.

As the reaction proceeds, the core shell silica particles can also become less transparent and more opaque, and the pH of the reaction solution decreases.

The core shell silica have adhesive properties when partially dried, for example, by air-drying.

Typically the second metal ion displaces the first metal ion from the metal silicate on the surface of the silica core. In one embodiment substantially all of the first metal ion is displaced.

The first metal ion is typically a monovalent ion, preferably a group 1 metal ion.

In an embodiment, the silica used can be any abrasive silica. The silica may be selected from the group consisting of a precipitated silica, a fumed silica and a fused silica.

Precipitated silica includes, but is not limited to Zeodent® 114 and Zeodent® 165 (precipitated silica particles produced by J.M. Huber—chemical name: synthetic amorphous silica), Sylodent® 783 produced by W.R. Grace, Sorbosil® AC-43 produced by Ineos (PQ Corp.)

The silica may be a fumed silica, such as Aerosil 200, produced by Evonik.

In another embodiment, the silica is a fused silica, which includes but is not limited to CAB-O-SIL® HP-60, produced by Cabot Corporation, TECO-SIL® 10 and TECO-SIL® 44css, produced by C-E Minerals, and Spheron P1500 made by the Japanese Glass Co.

Suitable silicas for use in the invention also include colloidal silicas (thickening silicas) having, such as the aerogels Syloid 244 and 266 (available from W. R. Grace Company), Aerosil (available from DeGussa Co.) and pyrogenic silicas sold under the tradename Cab-O-Sils (available from Cabot Corporation). Tixosil 333 and Tixosil 43B (available from Rhodia Ltda.), Zeodent 165 (available from J. M. Huber Corporation).

Other suitable silicas for use in the invention include silica abrasives which in turn include silica gels and precipitated amorphous silicas. These silicas are colloidal particles/particulates having an average particle size ranging from about 3 microns to about 12 microns, and more preferably between about 5 to about 10 microns and a pH range from 4 to 10 preferably 6 to 9 when measured as a 5% by weight slurry. Illustrative of silica abrasives useful in the practice of the present invention are marketed under the trade designation Sylodent XWA by Davison Chemical Division of W.R. Grace & Co., Baltimore, Md. 21203. Sylodent 650 XWA, a silica hydrogel composed of particulates of colloidal silica having a water content of 29% by weight averaging from about 7 to about 10 microns in diameter.

Other types of silica abrasives suitable for use in the invention include precipitated silicas having a mean particle size of up to about 20 microns, such as Zeodent 115, marketed by J.M. Huber Chemicals Division, Havre de Grace, Md. 21078, or Sylodent 783 marketed by Davison Chemical Division of W.R. Grace & Company.

The base may be in solid or aqueous form. The base is preferably selected from the group consisting of sodium hydroxide, potassium hydroxide, calcium hydroxide, barium hydroxide, ammonium hydroxide, sodium carbonate, potassium carbonate, trisodium phosphate, disodium phosphate, potassium phosphate, dipotassium phosphate, tetrasodium pyrophosphate, and tetrapotassium pyrophosphate, sodium silicate and potassium silicate. A particularly preferred base is sodium hydroxide or potassium hydroxide, most preferably 50% aqueous sodium hydroxide solution or 45% potassium hydroxide.

The process may be carried out at a temperature in the range of from 17° C. to 90° C. In one embodiment the process is carried out at room temperature. Room temperature, sometimes referred to as ambient temperature is typically from 20 to 26° C., and is the temperature achieved when no external heating of the reaction mixture is used. In another embodiment the process is carried out at a temperature of from 70 to 90° C. When preparing the core shell silica particles on an industrial scale, the mixer used to mix the reactants, such as a Lee mixer (Lee Industries), is preferably not heated up.

In one embodiment the base is sodium hydroxide and the process is carried out at a temperature of from 70 to 90° C. In another embodiment, the base is potassium hydroxide and the process is carried out at room temperature. This is embodiment is advantageous because the use of the more reactive potassium hydroxide means that heating is not required.

The formation of the core shell silica particles is typically complete after a time period of 2 hrs.

The weight ratio of the amount of base to the amount of silica particles may be from 1:1 to 1:20. The weight ratio for the amount of base to the amount of silica particles may be from 1:1 to 1:6, optionally about 1:4.

The turbidity of the core shell silica particles is decreased by increasing the weight ratio for the amount of base to the amount of silica particles.

An average depth of from 1 to 15 nm of silica may be removed from the surface of the silica particle to form the silica core, and metal silicate is formed on top of the silica core. The average depth of silica removed typically increases as the weight ratio for the amount of base to the amount of silica particles increases. The d(0.5) of the silica core may be from 1 to 15 nm less than the d(0.5) of the silica particles of the starting material. The d(0.5) of the silica core may be about 2 nm less than the d(0.5) of the silica particles of the starting material. The d(0.5) particle diameter of the silica core may be about 6 nm less than the d(0.5) of the silica particles of the starting material. There is a greater percentage reduction in particle diameter for rigid silica particles such as fumed silica than for porous silica particles such as high cleaning silica. For example, for fumed silica the percentage reduction in particle diameter (d(0.5)) may be approximately 15%, whilst for porous high cleaning silica the percentage reduction in particle diameter (d(0.5)) may be approximately 0.06%.

The second metal ion may be a divalent metal ion, a trivalent metal ion, a tetravalent metal ion or mixtures thereof. The second metal ion may be a group 2 metal ion, a transition metal ion, a group 13 metal ion, a group 14 metal ion or mixtures thereof. Preferably the second metal ion is $Ca^{2+}$, $Mg^{2+}$, $Zn^{2+}$, $Sn^{2+}$, $Sr^{2+}$, $Al^{3+}$, $Zr^{4+}$, $Ti^{4+}$, $Fe^{3+}$, $Fe^{2+}$, $Mo^{2+}$, $Co^{2+}$, $Ni^{2+}$, $Mn^{2+}$, $Cu^{2+}$, $Pd^{2+}$, $Mo^{2+}$, $Ru^{2+}$ or mixtures thereof.

The metal salt may be selected from the group consisting of a metal acetate, metal borate, metal butyrate, metal carbonate, metal halide, metal citrate, metal formate, metal gluconate, metal glycerate, metal glycolate, metal lactate, metal oxide, metal phosphate, metal picolinate, metal proprionate, metal salicylate, metal silicate, metal stearate, metal tartrate, metal undecylenate and mixtures thereof. The metal salt may be a metal chloride. The metal salt is preferably a zinc salt. The zinc salt may be selected from the group consisting of zinc acetate, zinc borate, zinc butyrate, zinc carbonate, zinc chloride, zinc citrate, zinc formate, zinc gluconate, zinc glycerate, zinc glycolate, zinc lactate, zinc oxide, zinc phosphate, zinc picolinate, zinc proprionate, zinc salicylate, zinc silicate, zinc stearate, zinc tartrate, zinc undecylenate and mixtures thereof. In a preferred embodiment the zinc salt is zinc chloride.

In one embodiment the silicate of the second metal ion comprises $ZnSiO_3 \cdot xH_2O$, wherein x is from 0 to 10.

In one embodiment, step i) occurs in the presence of a humectant. The weight ratio for the amount of humectant to water may be selected from a group of ratios consisting of 4:1 to 1:4; 3:1 to 1:3; 2:1 to 1:2; and 5:3 to 3:5. In general, the use of a humectant in the reaction process allows for the use of higher temperatures within the ranges described above.

The formation of the core shell silica particles of the invention described above can be effected by manipulating the amount of based used, the amount of humectant used, the amount of metal salt used, and varying the temperature of the reaction.

In an embodiment, the end point of the process results when the d(0.5) value of the core shell silica particles formed by the process is at least 5% greater in diameter than the d(0.5) value of the silica $(SiO_2)$ starting material. In another embodiment, the core shell silica particle is from 5%-10% greater in diameter than the average particle diameter of the silica starting material.

One of ordinary skill in the art can determine when the core shell silica particles of the invention have been obtained by several means, in addition to sampling the reaction mixture and testing the core shell silica particles formed until CSS particles with the requisite properties in terms of particle composition, layer formation and charge density have been formed.

The formation of the core shell particles can be monitored by determining the pH of the reaction mixture. In one embodiment, step i) is complete when the pH of the reaction mixture decreases by at least 0.5 pH units from the initial mixture of reactants. In another embodiment, step i) is complete when the pH of the reaction mixture decreases by at least 0.8 pH units from the initial mixture of reactants. Typically, step i) is complete when the pH of the reaction mixture is about 11. Typically, step ii) is complete when the pH of the reaction mixture is from 9 to 10. The process may comprise a further step iii) after step ii) of adjusting the pH of the reaction mixture to from 7 to 8. The pH of the reaction mixture is typically adjusted using acid. The acid may be selected from the group consisting of phosphoric acid, citric acid, malic acid and lactic acid. Phosphoric acid is preferred because it has minimal aftertaste.

In one embodiment of the process of the invention, soluble metal ions may be removed after step ii) or after step iii). The soluble metal ions may be removed by filtering the core shell silica particles to remove reactants and form solid core shell silica particles, and subsequently washing the core shell silica particles with deionized water. The core shell silica particles may be dried subsequently by heating, spray drying or freeze drying. The core shell silica particles formed may comprise from 0.0 to 0.5 weight % soluble metal ions. The soluble metal ions are preferably soluble zinc ions. As discussed above a low concentration of soluble metal ions, i.e. a low concentration of free metal ions such as zinc ions which can form complex with the CSS can be used to prepare oral care compositions with an improved taste profile.

The formation of the core shell particles can also be monitored by determining the conductivity of the reaction mixture. The end point of the process results when the conductivity of the reaction mixture decreases by at least 250 micro Siemens/cm (µS/cm) because the electric charges transfer from highly mobile ions (NaOH) to much less mobile silica surface (mobility≈0). In yet another embodiment, the end point of the process results when the conductivity of the reaction mixture decreases by 250-400 µS/cm. Typically, the core shell silica particles are formed when the conductivity of the reaction mixture decreases by at least 2 milliSiemens/cm (mS/cm). Usually, the core shell silica particles are formed when the conductivity of the reaction mixture decreases by at least 5 mS/cm.

In an embodiment, the core shell silica particles of the invention are formed when at least 1-6% of each of the silica particle starting material has been etched with one or more layers of silicate. In another embodiment, the core shell silica particles of the invention are formed when at least 2.5-5% of each of the silica particle starting material has been etched with one or more layers of $Na_2SiO_3$. In another embodiment, the core shell silica particles of the invention are formed when at least 3.5-4% of each of the silica particle starting material has been etched with one or more layers of silicate.

In an embodiment of the invention, the divalent, trivalent or tetravalent metal ion displaces 10%-90% of the monovalent metal ion of the Group I metal-CSS. In another embodiment of the invention, the divalent, trivalent or tetravalent metal ion displaces 20%-80% of the monovalent metal ion of the Group I metal-CSS. In an embodiment of the invention, the divalent, trivalent or tetravalent metal ion displaces 25%-65% of the monovalent metal ion of the Group I metal-CSS.

In an additional aspect, the present invention provides a core shell silica particle obtainable by a process as defined above.

Method of Using Compositions with Oral Care Compositions Comprising CSS

In a further aspect, the present invention provides a method of reducing or eliminating malodor in the oral cavity of a patient in need thereof, which comprises applying to the oral surfaces of the patient an oral care composition as defined above.

In one embodiment of the method, the patient is a mammal, which includes, but is not limited to humans and animals (e.g. dogs, cats, horses, cattle, sheep, llamas, etc.).

Another aspect of the invention is an oral care composition as defined above for use in reducing or eliminating malodor in the oral cavity of a patient in need thereof, which use comprises applying to the oral surfaces of the patient the oral care composition.

Embodiments of the present invention are further described in the following examples. The examples are merely illustrative and do not in any way limit the scope of the invention as described and claimed.

EXAMPLES

Example 1

The composition shown in Table 1 was used to produce the core shell silica particles of step i). Zeodent® 114 and Zeodent® 165 are precipitated silica particles produced by J.M. Huber (synthetic amorphous silica).

TABLE 1

Ingredients used in Example 1

| Ingredients | weight in grams |
| --- | --- |
| Sorbitol | 361.3 |
| Water | 43.8 |
| Zeodent ® 114 | 40.8 |
| Zeodent ® 165 | 40.2 |
| Solid NaOH | 4.0 |

Solid NaOH was first dissolved in water. Separately, sorbitol and silica particles (Zeodent® 114 and Zeodent® 165) were mixed in a Ross Pot for fifteen minutes, and the aqueous NaOH solution was added. The resulting dispersion was stirred at room temperature overnight, during which time the pH dropped from 10.71 to 9.74. The core shell silica particles obtained were semi-opaque in appearance. When these particles were dried for about ten minutes at room temperature, they acquired adhesive properties.

Example 2

The core shell particles were compared with other silica based particles. The compositions used are shown in Table 2.

TABLE 2

Ingredients used in Example 2

| | Weight in grams | | |
| --- | --- | --- | --- |
| Ingredient | Control #1 | Control #2 | Example 2 |
| Sorbitol | 0 | 360 | 360 |
| Water | 483 | 43 | 43 |
| Zeodent ® 114 | 80 | 80 | 80 |
| 50% NaOH | 0 | 0 | 8 |
| 100% Solid NaOH | 4 | 0 | 0 |

Without wishing to be bound by theory, it was believed that the particles produced in Control #1 did not have adhesive properties due to the lack of humectant (e.g., sorbitol) to keep the water on the silica particles, a preferred condition to ionize $SiO_2$.

Without wishing to be bound by theory, the particles produced in Control #2 also did not have adhesive properties because there was no NaOH to convert some of the $SiO_2$ into layers of $Na_2SiO_3$ covering the remaining $SiO_2$ core. In contrast, the core shell silica particles produced in Example 2 had adhesive properties similar to that of Example 1 above. These comparisons show that NaOH is needed, and water and/or humectant is/are preferable to obtain the core shell particles of the invention.

Example 3

In another comparative example, glycerin was substituted for sorbitol as the humectant component, and in two different weight ratios to water. The compositions prepared are shown in Table 3. Control #3 is similar to Example 1, but uses glycerin instead of sorbitol as the humectant and 8 g of 50% NaOH instead of 4 g of solid NaOH.

TABLE 3

Ingredients and Respective Weights Used in Control #3 and Example 3.

| Ingredient | Weight in grams | |
|---|---|---|
| | Control #3 | Example 3 |
| Glycerin | 361.3 | 252 |
| Water | 43.8 | 151 |
| Zeodent ® 114 | 40.8 | 80 |
| Zeodent ® 165 | 40.2 | 0 |
| 50% NaOH | 8 | 8 |

Without wishing to be bound by theory, the particles produced in Control #3 did not have adhesive properties likely because there was an insufficient amount of water to convert $SiO_2$ into $Na_2SiO_3$. In contrast, the core shell silica particles produced in Example 3 had adhesive properties.

Example 4

React $SiO_2$ abrasives with NaOH solution to create core-shell particles.

The reaction is: $2NaOH + SiO_2 \rightleftharpoons Na_2SiO_3 + H_2O$ 0.8% NaOH (50% solution) was used in clear silica colloids (see Table 4). When NaOH reacts with excess $SiO_2$, the pH will go beyond 11, then comes down gradually to below 10.0 (for toothpaste application, it requires the pH range between 6 and 10). The transition time is 6-24 hours at room temperature, but it may be much shorter by heating to higher temperature such as 75° C. What is happening in such $NaOH + SiO_2$ colloids? The optical properties of the colloids change during the reaction, from transparent to semi-opaque.

TABLE 4 making core-shell silica colloids (model colloids)

| Core-shell silica colloids | amount in grams | Control | amount in grams |
|---|---|---|---|
| Sorbitol | 359.8 | Sorbitol | 359.8 |
| Water | 43.2 | Water | 43.2 |
| Zeodent 114 | 80 | Zeodent 114 | 80 |
| mix for 30 minutes, clear colloids | | mix for 30 minutes, clear colloids | |
| 50% NaOH | 8 | | |
| Mix for several hours at room temperature, becomes semi-opaque | | | |

The optical appearance changes because the refractive index is changed on the shell. This makes sense because $SiO_2$ is known to be able to react with NaOH (or $Na_2CO_3$ or other strong bases) forming $Na_2SiO_3$, and the refractive index matched to $SiO_2$ (1.44-1.45) becomes mis-matched so the transparency is gone.

The present inventors postulated that the product of $NaOH + SiO_2$ is hydrated $Na_2SiO_3$ (refractive index is lower than SiO2, or $n_D < 1.44$). To confirm this hypothesis, a higher refractive index non-crystallizing sorbitol (refractive index=1.455-1.465) was used to increase the refractive index of aqueous solution (surrounding silica particles) to match the refractive index of core shell silica. It does turn back into a completely transparent colloid. This simple experiment evidences that the shell consists of low refractive index hydrated $Na_2SiO_3$ which is attached on the silica core. The inventors found a physical model for concentric rigid non-porous spherical particle light scattering to explain why colloids become opaque from transparent reactants.

Example 5

Physical Model for Core-Shell (Concentric) Particles Light Scattering

This model is based on "light Scattering by Small Particles", H. C. van de Hulst, 2003, pages 67-77.

The scattering intensity is proportional to the dielectric constant, $\alpha$.

For simple spherical particles:

$$\alpha = \frac{m^2 - 1}{m^2 + 2} \times a^3$$

Figure 3:
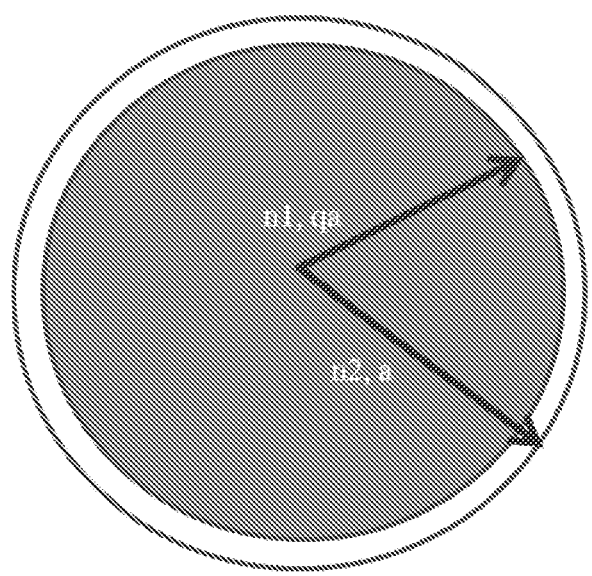
FIG. 3 shows a schematic of a core shell silica particle showing parameters used in the light scattering model described below.

Where:
 m=np/nm, where np and nm are the refractive indices of particle and water aqueous medium surrounding the particles (water+sorbitol+salts)
 a is the particle radius
For a concentric particle as shown in FIG. 3:
For the core particle, n1 is the refractive index, qa is the radius (q is the ratio of radius between core and shell).
For the shell, n2 is the refractive index, a is the radius
Where the refractive index (n) are defined as below:
 n=n1 for 0<r<qa
 n=n2 for qa<r<a
 n=1 for r>a (air for this case)
The dielectric constant for such core-shell (concentric) particle is: (depends on only 4 parameters only: n1, n2, and q, a)

$$\alpha = a^3 \times \frac{(n_2^2 - 1) \times (n_1^2 + 2n_2^2) + q^3(2n_2^2 + 1) \times (n_1^2 - n_2^2)}{(n_2^2 + 2) \times (n_1^2 + 2n_2^2) + q^3(2n_2^2 - 2) \times (n_1^2 - n_2^2)}$$

We can see the dielectric constant or light scattering intensity is different for simple spherical and concentric particles.

Example 6

Mid IR and Polarization Analysis

Mid IR spectroscopy was used to confirm the presence of silicate present on the shell layer of core silica. In all of the measurements, a three (multi) reflection ATR (Attenuated Total Reflectance) accessory was used to enhance the absorption spectrum from the samples. These accessories only allow light to penetrate 1-2 microns into the sample thus enhancing the signal from surface components compare with the bulk matrix. To further enhance the signal to noise, 32 scans were measured and averaged for each measurement.

The Mid IR fingerprint of silica and silicate are quite different and well resolved. Pure silica is characteristic of having a symmetric SiO vibration near 1074 cm−1 and a band around 960 cm$^{-1}$ due to the stretching vibration of SiOH bonds[1]. Silicates, on the other hand, have a prominent asymmetric shoulder vibration between 1200 cm$^{-1}$ and 1100 cm$^{-1}$. In addition, a strong asymmetric stretch, shifted from silica is found near 1000 cm$^{-1}$.

The ATR spectral fingerprint of core shell silica paste is greatly influenced by refractive index effects which can be large for inherently strong absorptions like Si—O stretching in silica and silicates. In transmission the Si—O band is near 1100 cm$^{-1}$ but in ATR it is typically around 1060 cm$^{-1}$. Also the bands are not totally symmetrical. Because these are pastes absorption is broad and potentially contains both amorphous/crystalline material.

In addition to regular ATR measurements, a Polarization Accessory was added to enhance our understanding and confirmation that a surface silicate species was present. The benefit of polarization measurement is that they give additional information on the molecular structure of a sample as it pertains to the crystallinity or molecular orientation. In this application, as the plane of polarized light orients along the sample plane, the ratio of silica to silicate should change. The polarization angles tested were: 0, 30, 60, 90, 120, 150, and 180 degrees. The spectral ratio of silicate (1022 cm$^{-1}$) to silica (1074 cm$^{-1}$) were calculated to demonstrate the presence of shell silicate. Table 5 shows the results from this analysis.

TABLE 5

| Polarization Angle | Ratio silicate/silica | |
|---|---|---|
| (degrees) | Zn-CSS | Ca-CSS |
| 0 | 1.093 | 1.138 |
| 30 | 1.092 | 1.124 |
| 60 | 1.053 | 1.103 |
| 90 | 1.024 | 1.06 |
| 120 | 1.038 | 1.081 |
| 150 | 1.073 | 1.126 |
| 180 | 1.094 | 1.139 |

The analysis shows an optimal concentration of silicate at 0 degrees when the plane of polarized light is positioned suggesting that the dipole moment change of silicate is located horizontal to the ATR surface.

Example 7

Etching of Silica by NaOH

CSS can be made from any kind of silica materials, for example rigid particles like fumed silica, or porous particles like amorphous dental silica abrasives: high cleaning silica Zeodent 105; regular silica like Zeodent 114, or thickening silica like Zeodent 165.

The amount of silica etched away depends on the BET specific area of the silica particles—particles with a greater surface area will be etched less deep. The amount of etching also depends on the ratio of silica to base. It was found that when the weight ratio of Zeodent 105 silica vs 50% NaoH solution=2.02 (endpoint), all silica dissolves. When we make Na-CSS toothpaste, 20% high cleaning silica (Zeodent 105) and 4.5% of 50% NaOH were used. So the ratio of SiO$_2$:50% NaOH=4.44:1. Since dissolved SiO$_2$:50% NaOH=2.02:1, so the remaining SiO$_2$ to NaOH (50%)= (4.44-2.02):1=2.42:1 after reaction. So the remaining SiO$_2$ vs initial SiO$_2$=2.42/4.44=54.55%, or volume change ($\Delta V/V$)=54.55%-100%=-45.45%. Note the endpoint for dissolving all silica material might vary from SiO$_2$ to SiO$_2$ (different silicas may have different endpoints, so for example the endpoint for fumed silica may not be 2.02:1).

Example 8

Calculation from BET Specific Surface Area

Calculation for all SiO$_2$ (including both rigid and porous particles) using BET specific surface area (S/W). For high cleaning silica (e.g. Zeodent 105, S/W=35 m$^2$/g and density d=2.2 g/cm$^3$), the change in particle diameter ($\Delta X$) is given by the following formula:

$$\Delta X = [(\Delta V/V)/(S/W)] \times 1/d$$
$$\Delta X = (-0.4545/35 \times 10^4 \text{ cm}^2/\text{g}) \times (1/2.2 \text{ g/cm}^3)$$
$$\Delta X = -5.90 \times 10^{-7} \text{cm}$$
$$\Delta X = -590 \text{ nm} (-0.590 \text{ }\mu\text{m})$$

Example 9

Calculation from Particle Diameter

This is calculation is useful for monodisperse, rigid, spherical particles. Since the particle outer surface area is very small (compared to microporous particles), the rigid particles will be etched much more relatively (higher percentage).

$$V = \frac{1}{6}\pi D^3$$

$$dV = \frac{1}{2}\pi D^2 dD$$

$$\frac{dV}{V} = 3 \times \frac{dD}{D} =$$

$$\frac{dD}{D} = -\frac{1}{3} \times \frac{dV}{V}$$

For a 12 nm fumed silica (e.g. Aeorsil 200), if dV/V=−0.4545 by assuming the same relative volume change ratio as high cleaning silica (e.g. Zeodent 105), the change in particle diameter $\Delta D$=−0.1515×12 nm=−1.8 nm. This change in diameter (−1.8 nm from a 12 nm silica) is proportionally greater than the high cleaning silica (−0.590 μm of a 10 μm silica=5.9%).

Example 10

Model for the Number of Layers of Na$_2$SiO$_3$ on Silica Surface Using ESCA Data X-ray from ESCA (XPS or X-ray Photospectroscopy) can penetrate down from surface to 10 nm deep. 1 layer of Silica or Na$_2$SiO$_3$ is ca. 1 A (0.1 nm). For Na$_2$SiO$_3$ molecule: Na/Si=2:1. So for 100 monolayers, Na/Si=0.02:1. But from ESCA data: Na/Si=0.084:1 Therefore there are 0.084/0.02=4.2≈4 layers of Na$_2$SiO$_3$.

Example 11

Model for the Number of Layers of Na$_2$SiO$_3$ on Silica Surface Using Raman Spectroscopy $$B1 = \frac{\text{Na2SiO3 weight (g)}}{\text{CSS Colloid total weight (g)}} \times$$

100% (determine $d$ by Raman Spectroscopy)

$$B2 = \frac{\text{Na2SiO3 weight (g)}}{\text{CSS colloid volume (cm}^3\text{)}} =$$

-continued $$B3 = \frac{Na2SiO3 \text{ weight (g)}}{CSS \text{ colloid weight (g)}} \times \frac{CSS \text{ colloid weight (g)}}{CSS \text{ colloid volume } (cm^3)} =$$

$$B1 \times CSS \text{ colloid density } (d)$$

$$B3 = \frac{Na2SiO3 \text{ weight (g)}}{\text{Silica surface } (cm^2)} = \frac{Na2SiO3 \text{ weight (g)}}{CSS \text{ colloid volume } (cm^3)} \times$$

$$\frac{CSS \text{ colloid volume } (cm^3)}{\text{Silica surface } (cm^2)} \times \frac{\text{Silica volume } (cm^3)}{\text{Silica volume } (cm^3)}$$

where:

$$\frac{\text{Silica surface } (cm^2)}{\text{Silica volume } (cm^3)} = \frac{4\pi r^2}{\frac{4}{3}\pi r^3} = \frac{3}{r}$$

$$\frac{\text{Silica volume } (cm^3)}{CSS \text{ colloid volume } (cm^3)} =$$

silica volume % ($\Phi$ %) determine from CSS recipe $$B3 = B2 \times \frac{r}{3} \times \frac{1}{\Phi\%} = B1 \times d \times \frac{1}{3} \times \frac{r}{\Phi\%}$$

$$B4 = \frac{\text{\# of Na2SiO3 molecules}}{\text{Silica surface area } (cm^2)} = \frac{B3}{Na2SiO3 M.W.} \times 6.023 \times 10^{23}$$

$$B5 = Na2SiO3 \text{ surface coverage } (\theta) =$$

$$\frac{\text{\# of Na2SiO3 molecules}}{\text{\# of SiO2 molecules}} =$$

$$\frac{B4}{\left(\frac{(1 \text{ cm} \times 10^8 \text{ A/cm})^2}{SiO2 \text{ molecule cross section area } (A^2)}\right)} =$$

$$\frac{B1 \times d \times \frac{1}{3} \times \frac{r}{\Phi\%}}{Na2SiO3 M.W.} \times \frac{6.023 \times 10^{23}}{\left(\frac{(1 \text{ cm} \times 10^8 \text{ A/cm})^2}{SiO2 \text{ molecule cross section area } (A^2)}\right)} =$$

$$\frac{3.5\% \times 1.189 \times \frac{5 \times 10^{-4} \text{cm}}{3 \times 8.13\%}}{122.06} \times \frac{6.023 \times 10^{23}}{\left(\frac{(1 \text{ cm} \times 10^8 \text{ A/cm})^2}{0.762 \text{ A}^2}\right)} = 32.1 \text{ layers}$$

Example 12

Zn-CSS colloid recipes are shown in Table 6:

TABLE 6

Zn-CSS colloid recipes and taste

| Sample ID | A9, positive control | A7Z4 | #18 | Negative control |
|---|---|---|---|---|
| Sorbitol | 360 | 360 | 3600 | 3600 |
| Water | 43 | 43 | 430 | 430 |
| Zeodent 114 | 80 | 80 | 800 | 80 |
| Zeodent 165 | 0 | 0 | 0 | 0 |
| 50% NaOH | 0 | 8 | 80 | 80 |
| added ZnCl2 | 5 | 5 | 5 | 0 |
| added ZnCl2, ppm | 10,000 | 10,000 | 10,000 | 0 |
| soluble ZnCl2, ppm | 5628 | 167 | 398 | 0 |
| Taste | Fail | Pass | Pass | Pass |

The pH of the reaction mixture initially jumps to approximately 12, and as the reaction continues the pH comes down to pH 9.5. For a reaction at room temperature, such pH changes need 24 hours; for a reaction temperature of 75° C., the reaction takes approximately 2 hours to finish.

From Table 6, for the A9 sample (positive control) with 10,000 ppm $ZnCl_2$ added, because no core-shell silica was formed (no NaOH was used), the soluble $ZnCl_2$ concentration was very high (5628 ppm) and the taste test failed. For samples A7Z4 and #18, 0.8% NaOH was used to make core-shell silica and the soluble $ZnCl_2$ decreased significantly to 167 ppm and 398 ppm, respectively. Both samples passed the taste test. This is thought to be due to the lower concentrations of soluble Zinc. The taste of the A7Z4 and #18 was the same as for the negative control with core-shell silica but without $ZnCl_2$ (the comment from the flavorist is quoted as "taste okay without noticeable metallic taste and astringency").

Example 13

To isolate the Zn-CSS abrasive, we filtered the colloidal solution by using filter paper and washed the wet Zn-CSS solid with water to remove the soluble Zn++:

TABLE 7

Isolation of Zn-CSS abrasive

| #93B | Gram | Percentage |
|---|---|---|
| Water | 2820.80 | 74.43% |
| Zeodent 105 | 562.00 | 14.83% |
| 50% NaOH | 226.50 | 5.98% |
| ZnCl2 | 180.41 | 4.76% |
| Sum | 3789.71 | 100.00% |

Synthesis procedure: Add water and 50% NaOH in a reaction container. Keep stirring with a mechanical stirrer (ca. 200 RPM). Heat up the aqueous solution above 100° C. steam water-bath to control the temperature at 80-90° C. Add Zeodent 105 high cleaning silica powder into the solution slowly. Keep stirring; react for 4 hours to make Na+-CSS colloids at ca. 85° C. Dissolve $ZnCl_2$ in 1000 cc hot water (75° C.). Add this $ZnCl_2$ solution into the above colloidal suspension slowly with stirring. Let react for 1 hour at ca. 85° C. Stop heating and cool down to room temperature. Keep stirring overnight. Use filter paper to filter the above colloids with vacuum. Collect the filtered liquid. Measure pH (6.287) and conductivity (91.0 mS/cm). Measure soluble Zn++ by EMD Quant® Zn++ test strip (20-50 ppm Zn++). Wash the Zn++-CSS wet solid using water to remove the soluble Zn++. Measure the soluble Zn++ until [Zn++]=0 ppm. Dry the Zn++-CSS solid at 110° C. overnight. Calculate yield (101.97%), which yield was slightly over 100% because there were some water moisture in the solid without complete evaporation during drying. Measure total Zn (14.32%) by atomic absorption method, which is close to the theoretical total Zn level (13.04%).

The total Zn level can be adjusted by changing the ratio of $SiO_2$ vs 50% NaOH. One example is shown in Table 8:

TABLE 8

Formulation to maximize total Zn level

| | Amount (g) | % |
|---|---|---|
| Water | 2847.40 | 80.39 |
| Zeodent 105 | 280.10 | 7.91 |
| 50% NaOH | 234.00 | 6.61 |
| $ZnCl_2$ | 180.39 | 5.09 |
| Total | 3541.89 | 100.00 |

In this recipe, $SiO_2$ is controlled in excess slightly as compared to 50% NaOH in terms of the number of moles. After reaction for 4 hours at 85° C., the initial opaque colloidal suspension became fully transparent. To find out why, the total Zn was determined by atomic absorption (17.63%), which was slightly less than the theoretical total Zn (21.81%) calculated from the above recipe. This indicates that most of the silica reacted with NaOH, the remaining silica formed smaller size core silica particles, resulting in the formation of transparent Zn++-CSS suspension (smaller particles scatter less light). It is believed that such small colloidal particles might be as small as commercial fumed silica particles (5-50 nm). In theory, maximum total Zn in Zn++-CSS should be less than the Zn level in pure $ZnSiO3$ (46.22%). Thus, the shell thickness or Zn % can be controlled by adjusting the ratio of $SiO_2$ vs NaOH.

Example 14

ESCA Analysis of Zn Core Shell Silica (Zn-CSS) Powder

ESCA (electron spectroscopy for chemical analysis) was used to determine the surface composition of Zn-CSS powders, prepared as described above. ESCA only analyzes the outer 10 nm of the sample surface, so it the ideal method for detection of Zn and silicate on the surface of the powder materials. The samples analyzed include both #93B and #94, which was prepared using the higher $NaOH/SiO_2$ ratio. Both materials were analyzed as prepared. The ESCA surface composition data for the Zn-CSS powders are shown in Table 9.

TABLE 9

ESCA Analysis of Zn-CSS

| | Atomic percentage | | | | | Atomic ratio | Si Peak (eV) |
|---|---|---|---|---|---|---|---|
| Sample | $O_{total}$ | Si | $O_{SiO3}$ | Na | Zn | Cl | Si/O | Si |
| $SiO_2$ (Zeodent 105) | 69.30 | 30.30 | | | | | 0.44 | 103.4 |
| 37.5% $Na_2SiO_3$ | 63.19 | 22.75 | 9.45 | 14.06 | | | 0.36 | 102.7 |
| Zn-CSS (#93B) | 64.16 | 26.52 | 7.35 | 3.18 | 4.65 | 1.49 | 0.41 | 103.1 |
| Zn-CSS (#94) | 62.35 | 25.09 | 11.78 | 4.39 | 6.34 | 1.82 | 0.40 | 103.0 |

The data reveal that a significant concentration of Zn is present on the surface of both the Zn-CSS materials. In addition, an oxygen peak that is characteristic of silicate ($O_{SiO3}$) was also observed in the data. This peak is not observed for $SiO_2$. Thus the detection of Zn and the presence of the $O_{SiO3}$ peak both suggest formation of Zn silicate on the silica surface. In addition, the concentration of Zn was higher for sample #94 than for #93B, confirming that the amount of surface Zn can be controlled by the Zn-CSS preparation procedure. Further evidence for silicate formation on the sample surfaces is apparent in the Si/O atomic ratios and Si peak positions for the two samples. The Si/O ratios for both samples have decreased relative to the silica standard and moved toward that for the sodium silicate reference. Also, the Si peak has shifted away from that for silica and toward that for silicate. These data are indicative of both silicate and silica in the materials. Sodium was also detected on the surfaces of both Zn-CSS samples, indicating that Na silicate is likely also present in the materials. The Na concentrations were lower than those for Zn, however. Finally a low amount of Cl was also observed for both materials, probably reflecting the presence of a low solubility Zn hydroxy chloride compound as an impurity.

Example 15

Synthesis of Zn-CSS Colloids with Freeze Drying

Table 10 shows a synthesis recipe for Zn-CSS. To isolate the Zn-CSS abrasive, the colloidal solution was filtered using filter paper, and the wet Zn-CSS solid was washed with water to remove the soluble $Zn^{2+}$.

TABLE 10

Synthesis of Zn-CSS colloid

| | actual weight, g | weight% |
|---|---|---|
| Water | 5666.00 | 78.25 |
| Zeodent 105 | 1120.00 | 15.53 |
| 50% NaOH | 447.00 | 6.21 |
| ZnCl2 | 360.41 | 4.99 |
| | 7593.41 | 100.00 |

Synthesis procedure: Add water and 50% NaOH in a reaction container. Keep stirring with a mechanical stirrer (ca. 200 RPM); heat up the aqueous solution above 100° C. steam water-bath to control the temperature at 80-90° C.; add Zeodent 105 high cleaning silica powder into the solution slowly. Keep stirring; react for 4 hours to make Na+-CSS colloids at ca. 85° C.; dilute the colloid with 1000 cc hot water (75 C) for better mixing before adding ZnCl2 solution; dissolve ZnCl2 in 1000 cc hot water (75° C.). Add this ZnCl2 solution into the above colloidal suspension slowly with stirring. Let react for 1 hour at ca. 85° C.; stop heating and cool down to room temperature. Keep stirring overnight; use filter paper to filter the above colloids with vacuum. Collect the filtered liquid. Measure pH (6.566) and conductivity (63.8 mS/cm). Measure soluble Zn++ (as is without dilution) by Zn++ test stripe (ca. 20 ppm); wash the Zn++-CSS wet solid by water to remove the soluble Zn++; dry the Zn++-CSS colloid to obtain dry Zn-CSS abrasive by dry freezing or pray drying; calculate yield (close to 100%), which yield was slightly over 100% because there were some water moisture in the solid without complete evaporation during drying.

Freeze Dry Procedure:

The filtered colloid is then mixed with DI water, the mass ratio between water and Zn-CSS is about 1:1. Freeze the mixture until it becomes solid. Turn on the freeze dryer to cool the chamber. When the temperature of the chamber drops down to −47° C., load the frozen sample into the chamber and turn on vacuum. The dried Zn-CSS powder was quantified later. Soluble $Zn^{2+}$=0.018% or 180 ppm in the solid. Total Zn=11.48%. The theoretical total Zn level is 13.04%. Residue water in the solid=11%

Example 16

ESCA (electron spectroscopy for chemical analysis) was used to determine the surface composition of the Zn-CSS powders, prepared as described above. ESCA only analyzes the outer 10 nm of the sample surface, so it is the ideal method for detection of Zn and silicate on the surface of powder materials. The ESCA surface composition data for the Zn-CSS powders are shown in Table 11.

TABLE 11

ESCA data for Zn-CSS abrasive compositions

| Sample | Atomic percentage | | | | | |
|---|---|---|---|---|---|---|
| | $O_{total}$ | Si | $O_{SiO3}$ | Na | Zn | Cl |
| $SiO_2$ (Zeodent 114) | 68.97 | 30.67 | | 0.36 | | |
| 37.5% $Na_2SiO_3$ | 63.19 | 22.75 | 9.45 | 14.06 | | |
| Zn-CSS (#93B) | 64.16 | 26.52 | 7.35 | 3.18 | 4.65 | 1.49 |
| Zn-CSS (#93B)—(3 × $H_2O$ rinse) | 64.79 | 26.60 | 6.92 | 2.63 | 4.89 | 1.10 |
| Zn-CSS—freeze dried | 63.13 | 26.22 | 6.07 | 3.82 | 4.50 | 2.34 |
| ZN-CSS—freeze dried (3 × $H_2O$ rinse) | 66.39 | 27.05 | 3.64 | 1.67 | 4.48 | 0.42 |

The data reveal that a significant concentration of Zn is present on the surface of the freeze dried Na-ZnCSS material. In addition, an oxygen peak that is characteristic of silicate ($O_{SiO3}$) was also observed in the data. This peak is not observed for $SiO_2$. Thus the detection of Zn and the presence of the $O_{SiO3}$ peak both suggest formation of Zn silicate on the silica surface. Sodium was also detected on the surface of the freeze dried Na-ZnCSS sample, indicating that Na silicate is likely also present in the material. As seen in Table 10, the atomic compositions (mainly total Zn and Na levels) of Na—Zn-CSS solid (#114) dried by freeze drying are very similar to the Na—Zn-CSS solid (#93B) dried by heating at 110 C in the oven. Thus, the freeze dry process was successful based on the analytical (total Zn and residual water levels) and ESCA data.

Example 17

Malodor Control Toothpaste

For non-CSS toothpaste, usually the toothpaste is made at room temperature, if CMC/Xanthan gum polymers are used, because polymer gum solution can form at room temperature. To make Zn2+-CSS tartar control toothpaste (Table 12), we first make $SiO_2/Na_2SiO_3$ core shell silica by heating water, NaOH, glycerin, and silica at 80-90° C. for 4 hours.

Then we add $ZnCl_2$ which will bring the pH to 9-10 and then further neutralize the pH to 7-8 by using acids such $H_3PO_4$, citric acid, or lactic acid. The rest of the synthesis is the same as for normal non-CSS toothpaste.

TABLE 12

Toothpaste recipes: Zn2+-CSS toothpaste (containing 1% and 2% ZnCl2) vs. non-CSS toothpaste.

| Ingredient | Comparative Example | CSS with malodor control | CSS with malodor control |
|---|---|---|---|
| Thickener | 0.7 | 0.8 | 0.6 |
| PEG 600 | 3 | 3 | 3 |
| Humectant | 35.946 | 33.638 | 33.788 |
| Sweetener | 0.3 | 0.3 | 0.3 |
| NaF | 0.32 | 0 | 0 |
| NaMFP | 0 | 0.76 | 0.76 |
| TKPP | 2.44 | 0 | 0 |
| STPP | 3 | 0 | 0 |
| 50% NaOH | 0.54 | 4.5 | 4.5 |
| ZnCl2, 97% | 0 | 1 | 2 |
| Sylodent VP5 | 22 | 0 | 0 |
| Zeodent 105 | 0 | 22 | 22 |
| Zeodent 165 | 4.5 | 4.5 | 4.5 |
| H3PO4 | 0 | 2 | 0.8 |
| water/SLS slurry | 5.17891 | 0 | 0 |
| SLS | 0 | 2 | 2 |
| Betaine | 1.25 | 0 | 0 |
| Flavor | 1.44 | 1.3 | 1.3 |
| water | 19.16509 | 24.2 | 24.2 |
| Blue Poly 50 | 0.2 | 0 | 0 |
| Blue-15(10%) glycerin slurry | 0.02 | 0 | 0 |
| FD&C Blue No. 1 dye | 0 | 0.002 | 0.002 |
| Timiron MP-149 (Mica) | 0 | 0 | 0.25 |
| | 100 | 100 | 100 |

Zn2+-CSS toothpaste synthesis procedure: Make Fluoride and saccharide water solution. Make CMC/Xanthan gums/PEG 600 solution. Put the Fluoride/saccharide solution, gum solution and Zn2+-CSS colloids in Ross pot. Add thickening silica (Zeodent 165) and blue dye. Mix for 30 min under full vacuum and high speed. Add SLS and flavor. Mix for 10 min under full vacuum.

$ZnCl_2$ is acidic and thus using more $ZnCl_2$ will require less acid to neutralize the pH to 7-8. The neutralizing acids have different aftertastes after brushing. Citric acid has a strong acidic aftertaste and lactic acid has a milky taste. $H_3PO_4$ tastes like soft drinks such as soda and is the best acid to use with little negative aftertaste. However, $H_3PO_4$ may potentially capture the Zn2+ from the Zn2+-CSS particle surface because the resulting $Zn_3(PO_4)_2$ is less soluble than $ZnSiO_3$. This process can be monitored by measuring the soluble Zn2+ concentration (in ppm) by using EMD Quant® Zn2+ test stripes (purchased from VWR co.) which measurement range is from 0 to 50 ppm. The toothpaste is diluted to 10% by water and the 10% Zn2+ level is measured by the Zn2+ test paper. If the 10% Zn2+=0 ppm, $H_3PO_4$ may chelate the Zn2+ from Zn-CSS particles during aging. For the above ZnCl2 toothpaste, 10% Zn2+≠(4-10 ppm for 1% ZnCl2 toothpaste and ca. 20 ppm for 2% ZnCl2 toothpaste).

It is possible to control the soluble Zn2+ concentration independently from the total Zn concentration. We have isolated the solid Zn2+-CSS abrasive. We can make soluble Zn2+ zero ppm by using this Zn2+-CSS solid abrasive which can be obtained by filtering out the reaction mixture (water, NaOH, $SiO_2$, and $ZnCl_2$), because the resulting solid Zn2+-CSS can be washed thoroughly to remove the soluble Zn2+ by water. We found the soluble Zn2+ concentration was zero ppm by using Zn2+ test strips when such filtered/washed solid Zn2+-CSS was used to make toothpaste. For optimal malodor performance, we may control soluble Zn2+ concentration by adding certain amount of soluble ZnCl2 into the solid Zn2+-CSS toothpaste.

Example 18

$Zn^{2+}$ Absorption by CSS

We designed a Langmuir absorption test method to determine how much $Zn^{2+}$ can be absorbed by the Na+-CSS toothpaste:
1) Weigh out 9 samples with 100 g of Na+-CSS toothpaste for each sample;
2) Weigh out 9 different amounts of $ZnCl_2$. Dissolve each $ZnCl_2$ powder sample in accurate amount of water;
3) Add ZnCl2 water solution to each toothpaste sample;
4) Analyze soluble $Zn^{2+}$ by atomic absorption
5) Plot $Zn^{2+}$ concentration (in ppm) added vs. $Zn^{2+}$ concentration detected (in ppm). Compare the curve vs. the theoretical straight line (dotted line, see FIG. 4). Their difference is the amount of $Zn^{2+}$ absorbed by the CSS particles in the toothpaste. The bigger the difference, the higher the $Zn^{2+}$-chelating ability for the Na+-CSS toothpaste.

TABLE 13

Zn2+ absorption: Zn-CSS toothpaste (TP) with 2% NaOH (50%) and 1% ZnCl2.

| TP (g) | ZnCl2 added (g) | total ZnCl2 (g) | Zn2+, ppm | Zn2+, detected, ppm |
|---|---|---|---|---|
| 100 | 0.13 | 1.13 | 5420 | 189 |
| 100 | 0.25 | 1.25 | 5995 | 338 |
| 100 | 0.52 | 1.52 | 7290 | 365 |
| 100 | 1.09 | 2.09 | 10024 | 178 |
| 100 | 2.06 | 3.06 | 14677 | 1927 |
| 100 | 4.04 | 5.04 | 24173 | 13180 |
| 100 | 6.19 | 7.19 | 34485 | 18174 |
| 100 | 8 | 9 | 43166 | 27951 |
| 100 | 9.9 | 10.9 | 52279 | 33015 |

Figure 4:
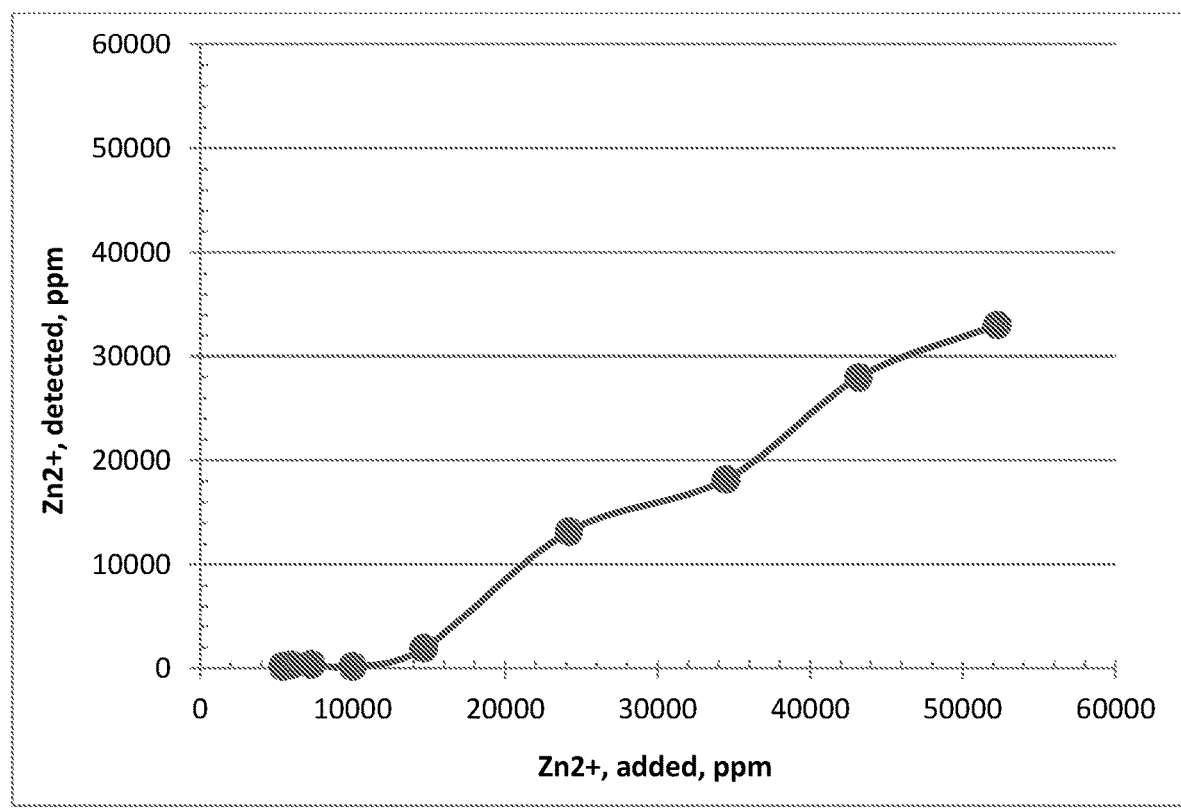
FIG. 4 shows a plot of $Zn^{2+}$ concentration (in ppm) added vs. $Zn^{2+}$ concentration detected (in ppm) for Zn-CSS.

FIG. 4 shows the plot for $Zn^{2+}$ absorption. We can see that the 1% $ZnCl_2$ toothpaste can chelate more $Zn^{2+}$ and the soluble $Zn^{2+}$ concentration is relatively small (below 400 ppm) when $ZnCl_2 \leq 2\%$ (total $Zn \leq 1\%$). Thus we can control soluble $Zn^{2+}$ close to zero when total $Zn \leq 1\%$. Too much $ZnCl_2$ (>2%) added in situ will cause a taste issue. However, if more total Zn is needed without a negative taste issue, we can concentrate the Zn level in the abrasive (Zn-CSS solid) as high as 17% by filtering the reaction mixture of water, NaOH, $SiO_2$ and $ZnCl_2$ and using such Zn-CSS abrasives to make toothpaste in a two-step process instead of a one-step in situ process.

Example 19

ESCA Analysis of Core Shell Silica (CSS) Powder Extracted from Toothpaste

ESCA (electron spectroscopy for chemical analysis) was used to determine the surface composition of silica/Zn-CSS powders extracted from three different toothpastes. Two of the toothpaste formulations were neutralized with $H_3PO_4$, while one used citric acid. ESCA only analyzes the outer 10 nm of the sample surface, so it is the ideal method for detection of Zn on the surface of the extracted silica materials. The silica was extracted from the pastes by dilution with deionized water. Six successive dilutions were made to remove the silica from the pastes and eliminate any water soluble components from the samples. The ESCA surface composition data for the CSS powders are shown in Table 14.

After the addition of zinc ion to the core shell silica particles, the surface charge density of the complex of core shell silica particles and zinc ion was calculated:

TABLE 14

Calculation of Surface Charge density and Ion Exchange Capacity

| 1% $ZnCl_2$ | 4800 ppm $Zn^{2+}$ |
|---|---|
| $Ca^{2+}$ absorption (max) | 8133 ppm $Ca^{2+}$ |
| each $Zn^{2+}$ and $Ca^{2+}$ contribute two electrons | |
| $Zn^{2+}$ | 0.000146834 mol/g in toothpaste |
| $Ca^{2+}$ | 0.000406650 mol/g in toothpaste |
| Sum of $Zn^{2+}$ and $Ca^{2+}$ | 0.000553484 |
| | $3.33 \times 10^{20}$ charges/g of toothpaste |
| use of 22% $SiO_2$ particles (diameter = 10 μm) | $1.52 \times 10^{21}$ charges/g of silica |
| volume of one silica spherical particle | $5.24 \times 10^{-10}/cm^3$ |
| density = 2.2 g/cm³ | $1.15 \times 10^{-9}$ g/particle |
| particles per 1 g of silica | $8.68 \times 10^{8}$ particles |
| | $1.75 \times 10^{12}$ charge/particle |
| | 0.00252 mol/g silica |
| Ion exchange capacity | 2.52 meq/g silica |

Given the amount of Zn2+ composition, and the average particle size, in a composition comprising 22% CSS particles of 10 μm average diameter (d(0.5)) with a substantially spherical shape, a value of $1.75 \times 10^{12}$ charge/particle was calculated, or 0.00252 mole/g silica which is 2.52 meq/g silica. Adjusting particle size will alter the amount of surface charge per particle. Accordingly, the preferred charge can be selected.

Example 20

Malodor: Zn-comprising CSS (see FIG. 1 for core-shell particle structure) can greatly reduce malodor comparable to a triclosan (anti-bacterial) containing toothpaste but, surprisingly, without a metallic Zn2+ taste. Gas Chromatography (GC) was utilized to determine the amount of reduction of volatile sulfur compounds (VSC) which are indicative of malodor. Head space samples were injected onto the GC for analysis. Test toothpaste samples were made into a 1:2 slurry of paste and water. 40 μL of the slurry was directly added to a headspace vial containing 3 mL of regular volatile sulfur compounds (VSC) (85% saliva, 10% water and 5% FTG) solution. The vials were then capped and incubated at 37 degrees overnight in a shaking water bath. All test formulations contained SLS (sodium lauryl sulfate) at 2%.

TABLE 15

Reduction in volatile sulfur compounds (VSC) by CSS and a complex of CSS with zinc.

| Product | % Reduction VSC | % of viable bacteria (from Resazurin anti-bacterial test) |
|---|---|---|
| Total ® | 98.19 | |
| no CSS 0% $ZnCl_2$ | 20.51 | |
| no CSS 1% $ZnCl_2$ | 99.11 | |
| no CSS 2% $ZnCl_2$ | 99.55 | |
| CSS + 0% $ZnCl_2$ | 23.17 | 2.34 |

TABLE 15-continued

Reduction in volatile sulfur compounds (VSC) by CSS and a complex of CSS with zinc.

| Product | % Reduction VSC | % of viable bacteria (from Resazurin anti-bacterial test) |
|---|---|---|
| Zn-CSS (CSS + ZnCl$_2$) | | |
| CSS + 0.1% ZnCl$_2$ | 22.19 | 3.58 |
| CSS + 0.25% ZnCl$_2$ | 21.21 | 3.89 |
| CSS + 0.5% ZnCl$_2$ | 31.51 | 6.27 |
| CSS + 1% ZnCl$_2$ | 92.87 | 4.48 |
| CSS + 2% ZnCl$_2$ | 95.68 | |

While CSS alone was able to reduce viable bacteria from the Resazurin test, the activity was not as effective as with complexes of CSS and zinc ions at higher concentrations (i.e. 1% or 2%) which were approximately as effective as a triclosan (anti-bacterial) containing toothpaste; thereby providing a viable alternative to using triclosan in toothpaste.

In addition, complexes of CSS and zinc ions at higher concentrations (i.e. 1% or 2%) were roughly comparable to non-CSS toothpaste containing 1% or 2% ZnCl$_2$ but which have very strong astringent Zn2+ taste.

The effectiveness of complexes of CSS and zinc ions (1% or 2%) in reducing VSCs was surprising given that a companion test of anti-bacterial activity showed that using lesser amount of ZnCl$_2$ (or not using ZnCl$_2$ at all) would result in better anti-bacterial activity.

Table 16 shows the result of experiments to determine the antibacterial activity of Zn-CSS particles. Toothpaste comprising Zn-CSS particles was diluted 1:1, 1:25 and 1:100 with tryptic soy broth (TSB) and the effect of the 3 compositions on bacterial cell viability were determined. The results show that the Zn-CSS colloids have an antibacterial effect at 1:1, 1:25 and even 1:100 dilutions, demonstrating that the CSS particles can be used as antibacterial agents not only in toothpaste, but also in diluted compositions such as mouthwash.

TABLE 16

| CSS toothpaste | Dilution factor with tryptic soy broth | Viability % |
|---|---|---|
| Comparative—Na-CSS (0.8% flavor; no ZnCl$_2$) | 1 | 2.31 |
| Zn-CSS (CSS + 0.1% ZnCl$_2$) | 1 | 1.40 |
| Zn-CSS (CSS + 0.25% ZnCl$_2$) | 1 | 2.43 |
| Zn-CSS (CSS + 0.5% ZnCl$_2$) | 1 | 2.63 |
| Zn-CSS (CSS + 1% ZnCl$_2$) | 1 | 2.28 |
| Comparative—Na-CSS (0.8% flavor; no ZnCl$_2$) | 25 | 0.47 |
| Zn-CSS (CSS + 0.1% ZnCl$_2$) | 25 | 0.09 |
| Zn-CSS (CSS + 0.25% ZnCl$_2$) | 25 | 0.81 |
| Zn-CSS (CSS + 0.5% ZnCl$_2$) | 25 | 0.75 |
| Zn-CSS (CSS + 1% ZnCl$_2$) | 25 | 1.80 |
| Comparative—Na-CSS (0.8% flavor; no ZnCl$_2$) | 100 | 3.19 |
| Zn-CSS (CSS + 0.1% ZnCl$_2$) | 100 | 5.57 |
| Zn-CSS (CSS + 0.25% ZnCl$_2$) | 100 | 2.93 |
| Zn-CSS (CSS + 0.5% ZnCl$_2$) | 100 | 4.75 |
| Zn-CSS (CSS + 1% ZnCl$_2$) | 100 | 4.67 |
| Negative control (no CSS or ZnCl$_2$) | 100 | 97.52 |

Example 22

Malodor Reduction by Zn-CSS

Zn-CSS compositions were compared to a triclosan-containing toothpaste, 1% ZnCl$_2$ and 2% ZnCl$_2$ for their effects on malodor reduction. 40 μl CSS was added to 3 g of saliva.

TABLE 17

| Composition | Malodor Reduction (%) |
|---|---|
| Triclosan containing toothpaste | 98.19 |
| 1% ZnCl$_2$ | 99.11 |
| 2% ZnCl$_2$ | 99.55 |
| Zn-CSS (1% ZnCl$_2$) | 92.87 |
| Zn-CSS (2% ZnCl$_2$) | 95.68 |

It can be seen from Table 17 that Zn-CSS provide malodor reduction which is comparable to a triclosan-containing toothpaste or ZnCl$_2$.

In order to see if there was an additional benefit related to the use of complexes of CSS and zinc ion, toothpaste compositions with different levels of ZnCl$_2$ were made and tested for the amount of soluble zinc.

TABLE 18

Soluble $Zn^{2+}$ (ppm) for toothpastes with different levels of $Zn^{2+}$.

| Sample | soluble $Zn^{2+}$ (ppm) |
|---|---|
| positive control, 1% ZnCl$_2$ | 5000 |
| CSS, negative control, 0% ZnCl$_2$ | 0 |
| CSS, 0.1% ZnCl$_2$ | 0 |
| CSS, 0.25% ZnCl$_2$ | 0 |
| CSS, 0.50% ZnCl$_2$ | 0 |
| CSS, 1% ZnCl$_2$ | 0 |

As can be seen from Table 18, the amount of $Zn^{2+}$ present in the 1% ZnCl$_2$ toothpaste resulted in the present of soluble zinc in amount of 5000 ppm. Given the presence of zinc and the known astringency (poor taste) of zinc, the complexes of the invention were able to avoid this astringency problem by chelating the zinc ion with the CSS particle (see also FIG. 1). The amount of soluble zinc in the CSS-containing complexes described in Table 18 above were confirmed by a flavorist who was unable to detect undesirable zinc taste.

Thus the new CSS particles of the invention have key advantages over current antibacterial/antimalodor agents for oral care compositions. Specifically, they provide an alternative antibacterial agent, which is useful because it is known that individuals can develop resistance to antibacterial compounds. Furthermore, the new CSS particles provide an improved taste profile over antibacterial agents such as zinc chloride.

As those skilled in the art will appreciate, numerous changes and modifications may be made to the embodiments described herein without departing from the spirit of the invention. It is intended that all such variations fall within the scope of the appended claims.

What is claimed is:
1. An oral care composition comprising:
a metal salt;
one or more core shell silica particle comprising:
a silica core, and
a surface layer etched with a metal silicate, the metal silicate comprising a potassium metal silicate and a zinc metal silicate; and an orally acceptable carrier,
wherein the potassium silicate and the zinc silicate of the one or more core shell silica particle are present in a weight ratio ranging from about 1:1 to about 1:4.

2. The oral care composition of claim 1, wherein the metal salt is a metal silicate.

3. The oral care composition of claim 1 further comprising a source soluble metal ions.

4. The oral care composition of claim 3, wherein the source of soluble metal ions is a multivalent metal ion.

5. The oral care composition of claim 3, wherein the source of soluble metal ions is a monovalent metal ion.

6. The oral care composition of claim 3, wherein the soluble metal ions is present in an amount up to 0.5 wt. %, based on the total weight of the oral care composition.

7. The oral care composition of claim 3, wherein the soluble metal ions comprises zinc ions.

8. The oral care composition of claim 1, wherein the surface of each particle has the general formula:

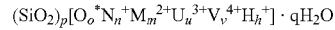

$$(SiO_2)_p[O_o^* N_n^+ M_m^{2+} U_u^{3+} V_v^{4+} H_h^+] \cdot qH_2O$$

wherein O* is oxygen in the silicate form; N is a monovalent metal ion; M is a divalent metal ion; U is a trivalent metal ion; V is a tetravalent metal ion; p, o, n, m, u, v, h and q are the atomic percentages of each component; and the total charge of each core shell silica particle is zero.

9. The oral care composition of claim 1, wherein the zinc comprises an amount of up to 20 wt. % of the total amount of metal.

10. The oral care composition of claim 1, wherein the silica core shell has a d(0.1) ranging from about 6 μm to about 9 μm, a d(0.5) ranging from about 18 μm to about 21 μm, and a d(0.9) ranging from about 41 μm to about 45 μm.

11. An oral care composition comprising:
one or more core shell silica particle comprising:
a silica core having a d(0.1) ranging from about 6 μm to about 9 μm, a d(0.5) ranging from about 18 μm to about 21 μm, and a d(0.9) ranging from about 41 μm to about 45 μm; and
a surface layer etched with at least two metal silicates; and
a thickener comprising carboxyvinyl polymer,
wherein the oral care composition has a pH from about 7 to about 10.

12. The oral care composition of claim 11, wherein at least one metal silicate is a monovalent metal silicate comprising potassium silicate.

13. The oral care composition of claim 12, wherein at least one metal silicate is a multivalent metal silicate comprising zinc metal silicate.

14. The oral care composition of claim 13, wherein the potassium silicate and the zinc silicate of the one or more core shell silica particle are present in a weight ratio ranging from about 1:1 to about 1:4.

15. The oral care composition of claim 12 further comprising a source soluble metal ions present in an amount up to 0.5 wt. %, based on the total eight of the oral care composition.

16. The oral care composition of claim 11, wherein the core shell silica particles have a surface charge density of from 0.5 to 4.5 meq/g silica.

17. The oral care composition of claim 11 further comprising a stannous ion source in an amount from about 0.01% to about 10%.

18. The oral care composition of claim 11 further comprising an amino acid selected from arginine, cysteine, leucine, isoleucine, lysine, alanine, asparagine, aspartate, phenylalanine, glutamate, glutamic acid, threonine, glutamine, tryptophan, glycine, valine, praline, serine, tyrosine, and histidine, and a combination of two or more thereof.

19. The oral care composition of claim 11 further comprising a humectant selected from glycerin, glycol, inositol, maltitol, mannitol, sorbitol, xylitol, propylene glycol, polypropylene glycol, polyethylene glycol, and a combination of two or more thereof.

20. The oral care composition of claim 11 further comprising a source of fluoride ions selected from stannous fluoride, sodium fluoride, potassium fluoride, amine fluoride, ammonium fluoride, stannous monofluorophosphate, sodium monofluorophosphate, potassium monofluorophosphate, potassium amine monofluorophosphate, ammonium monofluorophosphate, stannous fluorosilicate, sodium fluorosilicate, potassium fluorosilicate, amine fluorosilicate ammonium fluorosilicate, and a combination of two or more thereof.

* * * * *